United States Patent [19]

Böger et al.

[11] Patent Number: 5,026,730

[45] Date of Patent: Jun. 25, 1991

[54] ANILINOPHENYLTHIOUREAS, COMPOSITIONS CONTAINING THEM, AND THE USE THEREOF IN PEST CONTROL

[75] Inventors: Manfred Böger, Weil am Rhein, Fed. Rep. of Germany; Jozef Drabek, Oberwil; Josef Ehrenfreund, Allschwil, both of Switzerland

[73] Assignee: Ciba-Geigy Corporation, Ardsley, N.Y.

[21] Appl. No.: 230,814

[22] Filed: Aug. 11, 1988

[30] Foreign Application Priority Data

Aug. 21, 1987 [CH] Switzerland ............................ 3213/87
Jun. 21, 1988 [CH] Switzerland ............................ 2382/88

[51] Int. Cl.$^5$ .................... A01N 47/28; A61K 31/17
[52] U.S. Cl. .................... 514/586; 514/508; 514/629; 514/638; 558/4; 558/5; 564/27; 564/221; 564/222; 564/252
[58] Field of Search .................... 564/27; 514/586

[56] References Cited

U.S. PATENT DOCUMENTS

| | | | |
|---|---|---|---|
| 3,266,982 | 8/1966 | Popoff | 514/586 |
| 3,642,891 | 2/1972 | Teach | 564/27 |
| 3,781,290 | 12/1973 | Spaun et al. | 544/388 |
| 3,787,174 | 1/1974 | Kalopissis | 8/11 |
| 4,008,330 | 2/1977 | Yamamoto et al. | 514/586 |
| 4,328,247 | 5/1982 | Drabek | 424/320 |
| 4,623,662 | 11/1986 | De Vries | 514/586 |
| 4,812,466 | 3/1989 | Böger et al. | 514/351 |
| 4,897,424 | 1/1990 | Boger | 514/638 |

FOREIGN PATENT DOCUMENTS

| | | |
|---|---|---|
| 0282452 | 9/1988 | European Pat. Off. . |
| 0307361 | 9/1988 | European Pat. Off. . |
| 0296120 | 12/1988 | European Pat. Off. . |
| 0304025 | 2/1989 | European Pat. Off. . |
| 2174473 | 10/1973 | France . |
| 2465720 | 3/1981 | France . |
| 8605781 | 10/1986 | PCT Int'l Appl. . |
| 694940 | 6/1969 | South Africa . |
| 497402 | 11/1970 | Switzerland . |
| 1425789 | 2/1976 | United Kingdom . |
| 1537926 | 1/1979 | United Kingdom . |

Primary Examiner—Richard L. Raymond
Assistant Examiner—Scott C. Rand
Attorney, Agent, or Firm—Kevin T. Mansfield; Edward McC.Roberts

[57] ABSTRACT

The invention relates to novel substituted anilinophenylthioureas, anilinophenylisothioureas and anilinophenylcarbodiimides of formula I

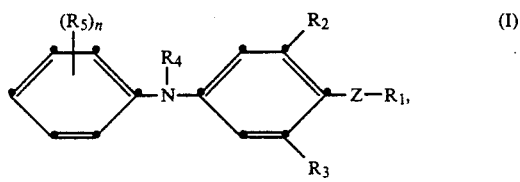

wherein $R_1$ is $C_1$-$C_{12}$alkyl, unsubstituted or substituted by one or more halogen atoms and/or $C_1$-$C_6$alkoxy groups; $C_3$-$C_8$cycloalkyl, unsubstituted or substituted by one or more $C_1$-$C_3$alkyl groups; or $C_3$-$C_8$cycloalkyl-$C_1$-$C_4$alkyl, $R_2$ and $R_3$ are each $C_1$-$C_5$alkyl or $C_5$-$C_6$cycloalkyl, $R_4$ is hydrogen, methyl or —CHO, $R_5$ is halogen; $C_1$-$C_4$alkyl, unsubstituted or substituted by one or more halogen atoms; $C_1$-$C_4$alkoxy, unsubstituted or substituted by one or more halogen atoms; or is a —CH═CH—$_2$, —CH$_2$—$_3$ or —CH$_2$—$_4$ bridge in 2,3- or 3,4-position, n is 0, 1, 2, 3 or 4, Z is —NH—CS—NH—, —N═C(SR$_6$)—NH— or —N═C═N—; and $R_6$ is $C_1$-$C_6$alkyl or allyl, to salts thereof with organic or inorganic acids, to the preparation of these compounds and to intermediates for their synthesis. The invention further relates to the use of the novel compound in pest control and to pesticidal compositions which contain at least one compound of formula I as active component. The preferred utility is the control of pests of animals and plants.

8 Claims, No Drawings

ANILINOPHENYLTHIOUREAS, COMPOSITIONS CONTAINING THEM, AND THE USE THEREOF IN PEST CONTROL

The present invention relates to novel substituted anilinophenylthioureas, anilinophenylisothioureas and anilinophenylcarbodiimides, to salts thereof with organic and inorganic acids, to their preparation and to intermediates for their preparation. The invention further relates to pesticidal compositions which contain these compounds and to the use thereof in pest control.

The compounds of this invention have the formula I

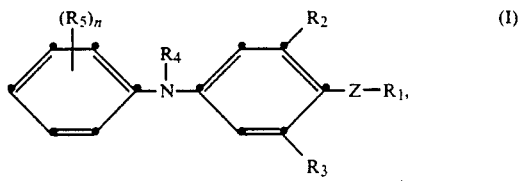

wherein
$R_1$ is $C_1$-$C_{12}$alkyl, unsubstituted or substituted by one or more halogen atoms and/or $C_1$-$C_6$alkoxy groups; $C_3$-$C_8$cycloalkyl, unsubstituted or substituted by one or more $C_1$-$C_3$alkyl groups; or $C_3$-$C_8$cycloalkyl$C_1$-$C_4$alkyl,
$R_2$ and $R_3$ are each $C_1$-$C_5$alkyl or $C_5$-$C_6$cycloalkyl,
$R_4$ is hydrogen, methyl or —CHO,
$R_5$ is halogen; $C_1$-$C_4$alkyl, unsubstituted or substituted by one or more halogen atoms; $C_1$-$C_4$alkoxy, unsubstituted or substituted by one or more halogen atoms; or is a $-(CH=CH)_2-$, $-(CH_2)_3-$ or $-(CH_2)_4-$ bridge in 2,3- or 3,4-position,
n is 0, 1, 2, 3 or 4,
Z is —NH—CS—NH—, —N=C($SR_6$)—NH— or —N=C=N—; and
$R_6$ is $C_1$-$C_6$alkyl or allyl.

Suitable halogen substituents are fluorine and chlorine as well as bromine and iodine. Fluorine and chlorine are preferred.

Alkyl groups can be straight chain or branched. Such alkyl groups may be, for example, methyl, ethyl, propyl, isopropyl, butyl, isobutyl, secbutyl, tert-butyl or pentyl, hexyl, octyl and the like, and isomers thereof.

Alkoxy groups may be straight chain or branched. Examples of such alkoxy groups are methoxy, ethoxy, propoxy, isopropoxy and butoxy and the isomers thereof.

Suitable $C_1$-$C_{12}$alkyl substituents which are substituted by one or more halogen atoms and/or $C_1$-$C_6$alkoxy groups can be straight chain or branched and be only partially halogenated or also perhalogenated and/or be substituted by 1 to 5 $C_1$-$C_6$alkoxy groups, the halogen and alkyl substituents being as defined above. Typical examples of such substituents are methyl which is substituted by 1 to 3 fluorine, chlorine and/or bromine atoms, for example $CHF_2$ or $CF_3$; ethyl which is substituted by 1 to 5 fluorine, chlorine and/or bromine atoms, for example $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl, each substituted by 1 to 7 fluorine, chlorine and/or bromine atoms, for example $CH_2CHBrCH_2Br$, $CF_2CHFCF_3$, $CH_2CF_2CF_3$ or $CH(CF_3)_2$; butyl or an isomer thereof which is substituted by 1 to 9 fluorine, chlorine and/or bromine atoms, for example $CF(CF_3)CHFCF_3$ or $CH_2(CF_2)_2CF_3$; methoxymethyl, methoxyethyl, ethoxyethyl, methoxypropyl, ethoxypropyl, propoxypropyl, methoxybutyl, ethoxybutyl, propoxybutyl or butoxybutyl, 1,2-dimethoxyethyl, 1,3-dimethoxyethyl, 1,3-dimethoxypropyl or 2,4-dimethoxybutyl.

Cycloalkyl groups may be, for example, cyclopropyl, cyclobutyl, cyclopentyl or cyclohexyl. The cycloalkyl groups can be substituted by one or more $C_1$-$C_3$alkyl groups and/or be linked to the remainder of the molecule through a $C_1$-$C_4$alkylene bridge.

Compounds of formula I, wherein Z is —N=C($SR_6$)—NH—, can also be in the form of acid addition salts. Acids suitable for forming such salts are organic as well as inorganic acids. Examples of such acids are: hydrochloric acid, hydrobromic acid, hydriodic acid, nitric acid, different phosphoric acids, sulfuric acid, acetic acid, propionic acid, butyric acid, valeric acid, oxalic acid, malonic acid, succinic acid, malic acid, maleic acid, fumaric acid, lactic acid, tartaric acid, citric acid, benzoic acid, phthalic acid, cinnamic acid, phenylsulfonic acid and salicylic acid.

Compounds of formula I, wherein Z is —N=C($SR_6$)—NH—, can be obtained in their tautomeric forms

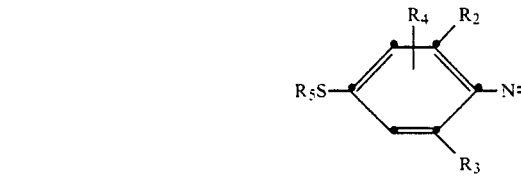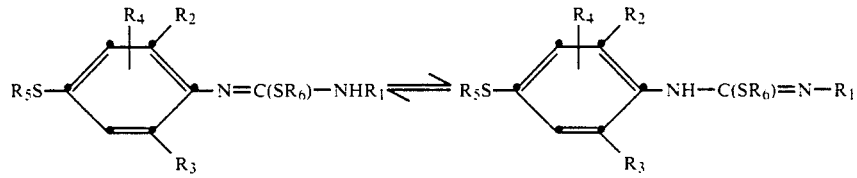

The invention encompasses the individual tautomers as well as mixtures of tautomers.

Depending on the value of n, the phenyl radical substituted by $R_5$ can be substituted by more than one $R_5$. If n is greater than 1, the different substituents $R_5$ can have the same or different meanings.

Preferred compounds of formula I are those wherein $R_1$ is $C_1$-$C_8$alkyl unsubstituted or substituted by one or more halogen atoms and/or $C_1$-$C_5$alkoxy groups, or is $C_3$-$C_8$cycloalkyl; $R_2$ is $C_1$-$C_5$alkyl; $R_3$ is $C_1$-$C_5$alkyl or $C_5$-$C_6$cycloalkyl; $R_4$ is hydrogen, methyl or —CHO; $R_5$ is halogen, $C_1$-$C_3$alkyl or a $-(CH=CH)_2-$ or $-(CH_2)_3-$ bridge in 2,3- or 3,4-position; n is 0, 1 or 2; Z is —NH—CS—NH—, —N=C($SR_6$)—NH— or —N=C=N—; and $R_6$ is $C_1$-$C_4$alkyl or allyl.

Among these compounds, those compounds of formula I are preferred in which
(a) $R_1$ is $C_1$-$C_5$alkyl or cyclopentyl; $R_2$ and $R_3$ are each $C_1$-$C_4$alkyl; $R_4$ is hydrogen, methyl or —CHO; $R_5$ is methyl; n is 0 or 1; and Z is —NH—CS—NH—; or
(b) $R_1$ is $C_1$-$C_5$alkyl or cyclopentyl; $R_2$ and $R_3$ are each $C_1$-$C_4$alkyl; $R_4$ is hydrogen, methyl or —CHO; $R_5$ methyl; n is 0 or 1; Z is —N=C($SR_6$)—NH—; and $R_6$ is $C_1$-$C_4$alkyl; or (c) $R_1$ is $C_1$-$C_5$alkyl or cylcopentyl; $R_2$ and $R_3$ are each $C_1$-$C_4$alkyl; $R_4$ is hydrogen, methyl or —CHO; $R_5$ is methyl; n is 0 or 1; and Z is —N=C=N—.

The compounds of formula I of this invention can be prepared by methods which are known per se, for example by (A) reacting an isothiocyanate of formula II

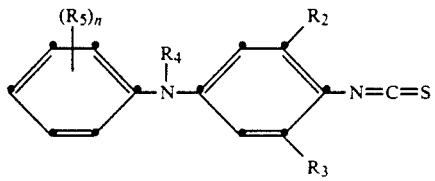

with an amine of formula III $H_2N-R_1$ (III)

to give the thiourea and, if desired, (B) reacting the resultant thiourea with a compound of formula IV $X-R_6$ (IV)

to give the isothiourea, or (C) converting the resultant thiourea into the carbodiimide by removal of hydrogen sulfide. In the formulae above, $R_1$, $R_2$, $R_3$, $R_4$, $R_5$, $R_6$ and n have the given meanings and X is a suitable leaving group, for example a halogen atom, preferably a chlorine, bromine or iodine atom, or is alkyl sulfate.

Process (A) is usually carried out under normal pressure and in the presence of an organic solvent or diluent. The reaction temperature is in the range from 0° to 150° C., preferably from 10° to 70° C. Examples of suitable solvents or diluents are: ethers and ethereal compounds such as diethyl ether, dipropyl ether, dibutyl ether, dioxane, dimethoxyethane and tetrahydrofuran; N,N-dialkylated carboxamides; aliphatic, aromatic and halogenated hydrocarbons such as benzene, toluene, xylenes, chloroform, methylene chloride, carbon tetrachloride and chlorobenzene; nitriles such as acetonitrile or propionitrile; and ketones, such as acetone, methyl ethyl ketone, methyl isopropyl ketone, methyl isobutyl ketone and cyclohexanone.

Process (B) is conveniently carried out in an inert organic solvent and under slightly elevated or normal pressure. The reaction temperature is in the range from 10° to 250° C., but is preferably the boiling temperature of the solvent employed or from 50° to 150° C. Examples of suitable solvents or diluents are: ethers and ethereal compounds such as diethyl ether, diisopropyl ether, dioxane and tetrahydrofuran; aromatic hydrocarbons such as benzene, toluene and xylenes; ketones such as acetone, methyl ethyl ketone and cyclohexanone; alcohols or dimethyl formamide.

Process (C) is conveniently carried out in an aprotic organic solvent or diluent and under normal pressure. The reaction temperature is in the range from 0° to 150° C., preferably from 10° to 50° C. Examples of suitable solvents or diluents are: ethers and ethereal compounds such as diethyl ether, dipropyl ether, dibutyl ether, dioxane, dimethoxyethane and tetrahydrofuran; N,N-dialkylated carboxamides; aliphatic, aromatic and halogenated hydrocarbons such as benzene, toluene, xylenes, chloroform, methylene chloride, carbon tetrachloride and chlorobenzene; nitriles such as acetonitrile and propionitrile; and ketones, e.g. acetone, methyl ethyl ketone, methyl isopropyl ketone, methyl isobutyl ketone and cyclohexanone. The removal of hydrogen sulfide is effected by methods which are described in the literature [T. Shibanuma, Chemistry Letters (1977), pp. 575-6; S. Kim, Tetrahedron Letters (1985), pp. 1661-1664; W. Weith, B. 6 (1873) 1398; G. Amiard, Bull. Soc. chim. 1956, 1360]. Suitable reagents for the elimination reaction are .e.g. HgO, specific pyridinium salts, chloroacetates, cyanuric chloride, p-toluene-sulfochloride or specific phosphate derivatives.

The isothiocyanates of formula II can be prepared by methods which are known per se, for example by thiophosgenating an aminodiphenylamine of formula V

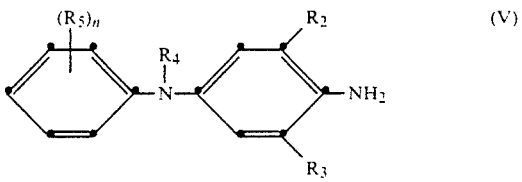

wherein $R_2$, $R_3$, $R_4$, $R_5$ and n are as defined for formula I.

The process for the preparation of the compounds of formula II is conveniently carried out in the presence of an organic or inorganic base, for example triethylamine or calcium carbonate, and of an inert solvent or diluent under normal pressure. The reaction temperature is in the range from 0° to 100° C. and is preferably the boiling temperature of the solvent or diluent employed or is in the range from 20° to 80° C. Suitable solvents and diluents are, for example, ethers or ethereal compounds such as diethyl ether, diisopropyl ether, dioxane or tetrahydrofuran; aromatic hydrocarbons such as benzene, toluene or xylenes; ketones such as acetone, methyl ethyl ketone or cyclohexanone; or chlorinated hydrocarbons such as dichloromethane. The process can also be carried out in the presence of water in a two-phase system.

Another means of preparing the isothiocyanates of formula II is via the corresponding thiourea which is unsubstituted at one nitrogen. This process comprises reacting an aniline of formula V with ammonium thiocyanate, in acidic medium preferably containing a mineral acid, to give the corresponding thiourea which, in turn, splits off ammonia on being heated to 130°-200° C. and is converted into an isothiocyanate of formula II (q.v. Saul Patai, "The Chemistry of Cyanates and their Thio Derivatives", John Wiley and Sons, 1977, p. 1032 et seq.; Chemistry and Industry, July 3, 1954, p. 735, J. N. Baxter et al., "New method of preparation of aryl isothiocyanates").

The aminodiphenylamines of formula V can be prepared by methods which are known per se, for example by reacting an aniline of formula VI

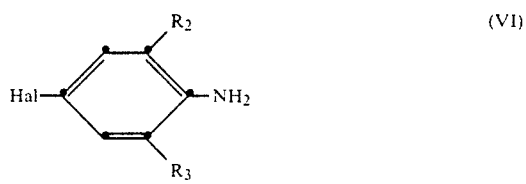

with a formanilide of formula VII

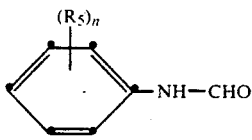

in which formulae $R_2$, $R_3$, $R_5$ and n are as defined for formula I and Hal is halogen, preferably chlorine or bromine. These N-formylamino-diphenyl-amines can be converted into the corresponding N-unsubstituted aminodiphenylamines ($R_4=H$) by heating in alkaline solution, or into the corresponding N-methylaminodiphenylamines ($R_4=CH_3$) by reduction, for example with a borane/methyl sulfide complex (Tetrahedron Letters, Vol. 23, No. 33, pp. 3315-3318) or by catalytic hydrogenation using customary hydrogenation catalysts, preferably rhenium oxides.

The process for the preparation of the aminodiphenylamines of formula V is preferably carried out in analogy to the Goldberg diphenylamine synthesis (J. Amer. Chem. Soc., 1928, 50, 859) in the temperature range from 150° to 180° C. and in the presence of a heavy metal catalyst, for example copper powder.

The compounds of formulae II and V are novel and likewise constitute an object of the invention. On the other hand, the compounds of formulae III, IV, VI and VII are known or can be prepared by methods which are known per se.

Surprisingly, it has been found that the compounds of formula I of this invention are valuable pesticides while being well tolerated by warmblooded animals and plants. The compounds of formula I are therefore suitable e.g. for controlling pests of animals and plants. Such pests belong principally to the phylum of Arthropoda, such as in particular insects of the orders Lepidoptera, Coleoptera, Homoptera, Heteroptera, Diptera, Thysanoptera, Orthoptera, Anoplura, Siphonaptera, Mallophaga, Thysanura, Isoptera, Psocoptera or Hymenoptera and arachnids of the order Acarina, e.g. mites and ticks. Every development stage of the pests can be controlled, i.e. the adults, pupae and nymphs, and also in particular the larvae and eggs. It is thus possible to control effectively in particular larvae and eggs of phytopathogenic insect pests and mites in crops of ornamentals and useful plants, for example in fruit and vegetable crops. If compounds of formula I are ingested by imagines, then a direct kill of the pests or a reduced oviposition and/or hatching rate can be observed. This last activity can be observed in particular in Coleoptera. In the control of pests that are parasites of animals, in particular of domestic animals and productive livestock, the chief pests are ectoparasites, such as mites and ticks and Diptera, for example *Lucilia sericata*.

The good pesticidal activity of the compounds of formula I corresponds to a mortality of at least 50-60% of the above pests.

The activity of the compounds of formula I and of the compositions containing them can be substantially broadened and adapted to prevailing circumstances by addition of other insecticides and/or acaricides. Examples of suitable additives include: organophosphorus compounds, nitrophenols and derivatives thereof, formamidines, ureas, carbamates, pyrethroids, chlorinated hydrocarbons, and *Bacillus thuringiensis* preparations.

The compounds of formula I are used in unmodified form, or preferably together with the inert, agriculturally acceptable adjuvants conventionally employed in the art of formulation, and can therefore be formulated in known manner to emulsifiable concentrates, directly sprayable or dilutable solutions, dilute emulsions, wettable powders, soluble powders, dusts, granulates, and also encapsulations in e.g. polymer substances. As with the compositions, the methods of application such as spraying, atomising, dusting, scattering or pouring, are chosen in accordance with the intended objectives and the prevailing circumstances.

The formulations, i.e. the compositions, preparations or mixtures containing the compound (active ingredient) of formula I or combinations thereof with other insecticides or acaricides, and, where appropriate, a solid or liquid adjuvant, are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, or of combinations thereof with other insecticides or acaricides, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$-$C_{22}$), e.g. the sodium or potassium salts of oleic or stearic acid, or of natural fatty acid mixtures which can be obtained e.g. from coconut oil or tall oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, castor oil thioxilate, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp., Ridgewood, N.J., 1979; Dr. Helmut Stache, "Tensid Taschenbuch" (Handbook of Surfactants), Carl Hanser Verlag, Munich/Vienna, 1981.

The pesticidal compositions usually contain 0.1 to 99%, preferably 0.1 to 95%, of a compound of formula I or a combination thereof with other insecticides or acaricides, 1 to 99.9% of a solid or liquid adjuvant, and 0 to 25%, preferably 0.1 to 20%, of a surfactant.

Whereas commercial products are preferably formulated as concentrates, the end user will normally employ diluted formulations of substantially lower concentration.

The compositions may also contain further ingredients, such as stabilisers, antifoams, viscosity regulators, binders, tackifiers as well as fertilisers or other active ingredients for obtaining special effects.

EXAMPLE 1

Preparation 1.1. Intermediates 1.1.1. 4-(N-Phenyl-N-formylamino)anilines 1.1.1.1. 2,6-Diethyl-4-(N-phenyl-N-formylamino)anilines A mixture of 36.3 g formanilide, 70 g of 2,6-diethyl-4-bromaniline, 42.0 g of potassium carbonate and 1 g of copper powder is stirred for 16 hours at 160° C. under nitrogen. To the cooled reaction mixture are then added 200 ml of toluene and 200 ml of water. After filtration over kieselguhr, the toluene phase is separated, dried over sodium sulfate and concentrated by evaporation. The residue is taken up in a 80:20 mixture of hexane/ethyl acetate and filtered over kieselguhr. The filtrate is concentrated by evaporation, and the residue is crystallised from isopropanol. The product is isolated by filtration and washed with hexane, to give the title compound of formula

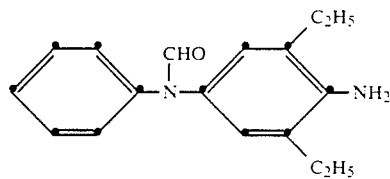

(compound 1.1.1.1.)

in the form of a beige-coloured powder which melts at 105°–107° C.

The following compounds are prepared in corresponding manner:

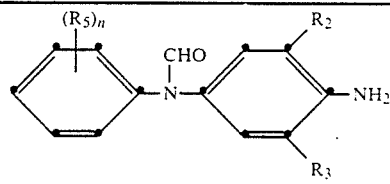

| Compound | $R_2$ | $R_3$ | $R_5$ | n | m.p. °C. |
|---|---|---|---|---|---|
| 1.1.1.2. | $CH_3$ | $CH_3$ | — | 0 | 134–136 |
| 1.1.1.3. | $CH_3$ | $C_2H_5$ | — | 0 | 88–90 |
| 1.1.1.4. | $C_2H_5$ | $CH(CH_3)C_2H_5$ | — | 0 | 80–82 |
| 1.1.1.5. | $CH(CH_3)_2$ | $CH(CH_3)_2$ | — | 0 | 127–129 |
| 1.1.1.6. | $C_2H_5$ | $C_2H_5$ | 4-$CH_3$ | 1 | 72–74 |
| 1.1.1.7. | $C_2H_5$ | $C_2H_5$ | 4-Cl | 1 | 88–89 |
| 1.1.1.8. | $CH(CH_3)_2$ | $CH(CH_3)_2$ | 4-Cl | 1 | 124–126 |
| 1.1.1.9. | $CH(CH_3)_2$ | cyclopentyl | — | 0 | 81–82.5 |

-continued

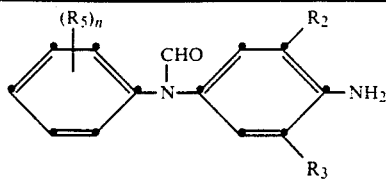

| Compound | R₂ | R₃ | R₅ | n | m.p. °C. |
|---|---|---|---|---|---|
| 1.1.1.10. | CH(CH₃)₂ | CH(CH₃)₂ | 4-F | 1 | 110–111 |
| 1.1.1.11. | CH(CH₃)₂ | CH(CH₃)₂ | 4-C(CH₃)₃ | 1 | 143–144 |
| 1.1.1.12. | C₂H₅ | CH(CH₃)₂ | 4-Cl | 1 | 112–113 |
| 1.1.1.13. | CH(CH₃)₂ | CH(CH₃)₂ | 3,4-Cl₂ | 2 | 137–139 |
| 1.1.1.14. | CH(CH₃)₂ | CH(CH₃)₂ | 4-OCH₃ | 1 | 120–121 |
| 1.1.1.15. | C₂H₅ | CH(CH₃)₂ | — | 0 | 102–104 |
| 1.1.1.16. | CH(CH₃)₂ | CH(CH₃)₂ | 4-CH₃ | 1 | 128–130 |
| 1.1.1.17. | CH(CH₃)₂ | CH(CH₃)₂ | 3-F | 1 | 103–104 |
| 1.1.1.18. | CH(CH₃)₂ | CH(CH₃)₂ | 2-F | 1 | 107–108 |
| 1.1.1.19. | CH(CH₃)₂ | CH(CH₃)₂ | 3-Cl | 1 | 100–102 |
| 1.1.1.20. | CH(CH₃)₂ | CH(CH₃)₂ | 4-CF₃ | 1 | 113–114 |
| 1.1.1.21. | CH(CH₃)₂ | CH(CH₃)₂ | 2,4,6-(CH₃)₃ | 3 | 173–175 |
| 1.1.1.22. | CH(CH₃)₂ | CH(CH₃)₂ | 2,3-(CH=CH)₂ | 2 | 101–103 |
| | CH₃ | CH(CH₃)₂ | — | 0 | |
| | C₂H₅ | cyclopentyl | — | 0 | |
| | C₂H₅ | cyclohexyl | — | 0 | |
| | CH(CH₃)₂ | CH(CH₃)₂ | 4-OCF₃ | 1 | |
| | C₂H₅ | C₂H₅ | 4-OCH₃ | 1 | |
| | C₂H₅ | C₂H₅ | 4-F | 1 | |
| | C₂H₅ | C₂H₅ | 4-O(CH₂)₃CH₃ | 1 | |
| | C₂H₅ | C₂H₅ | 4-CH(CH₃)₂ | 1 | |
| | C₂H₅ | C₂H₅ | 3-Cl | 1 | |
| | C₂H₅ | C₂H₅ | 3,4-Cl₂ | 2 | |
| | C₂H₅ | C₂H₅ | 3,4-(CH₃)₂ | 2 | |

1.1.2. 4-Aminodiphenylamines 1.1.2.1. 2,6-Diethyl-4-(N-phenylamino)aniline

A mixture of 6.8 g of 2,6-diethyl-4-N-phenylamino)aniline, 60 ml of 10% aqueous sodium hydroxide solution and 5 ml of polyethylene glycol (mol. wt. 200) is stirred for 2 hours at 100° C. The cooled reaction mixture is extracted with 150 ml of toluene and the separated organic phase is washed three times with water, dried over sodium sulfate and concentrated by evaporation. The residue is recrystallised from a mixture of toluene/hexane, affording the title compound of formula

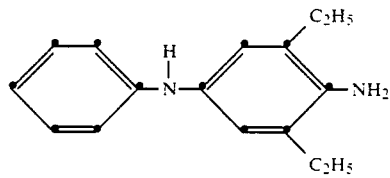

(compound 1.1.2.1.)

in the form of a beige-coloured powder which melts at 42°–44° C.

The following compounds are prepared in corresponding manner:

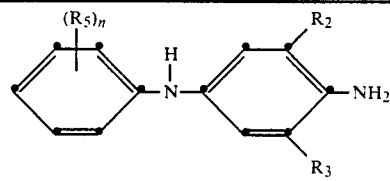

| Compound | R₂ | R₃ | R₅ | n | m.p. °C. |
|---|---|---|---|---|---|
| 1.1.2.2. | CH(CH₃)₂ | CH(CH₃)₂ | — | 0 | 95–96 |
| 1.1.2.3. | CH₃ | CH₃ | — | 0 | 79–81 |
| | CH₃ | C₂H₅ | — | 0 | |
| | C₂H₅ | CH(CH₃)₂ | — | 0 | |
| | C₂H₅ | CH(CH₃)C₂H₅ | — | 0 | |
| | CH₃ | CH(CH₃)₂ | — | 0 | |
| | C₂H₅ | cyclopentyl | — | 0 | |
| | C₂H₅ | Cyclohexyl | — | 0 | |
| | CH(CH₃)₂ | CH(CH₃)₂ | 4-OCF₃ | 1 | |
| | C₂H₅ | C₂H₅ | 4-Cl | 1 | |
| | C₂H₅ | C₂H₅ | 4-OCH₃ | 1 | |
| | C₂H₅ | C₂H₅ | 4-F | 1 | |
| | C₂H₅ | C₂H₅ | 4-O(CH₂)₃CH₃ | 1 | |
| | C₂H₅ | C₂H₅ | 4-CH(CH₃)₂ | 1 | |
| | CH(CH₃)₂ | CH(CH₃)₂ | 4-Cl | 1 | |
| | C₂H₅ | C₂H₅ | 3-Cl | 1 | |

-continued

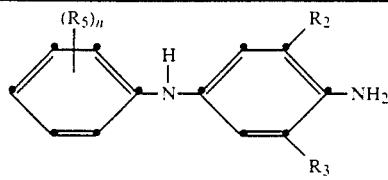

| Compound | R$_2$ | R$_3$ | R$_5$ | n | m.p. °C. |
|---|---|---|---|---|---|
| | C$_2$H$_5$ | C$_2$H$_5$ | 3,4-Cl$_2$ | 2 | |
| | C$_2$H$_5$ | C$_2$H$_5$ | 3,4-(CH$_3$)$_2$ | 2 | |
| | CH(CH$_3$)$_2$ | cyclopentyl | — | 0 | |
| | CH(CH$_3$)$_2$ | CH(CH$_3$)$_2$ | 4-F | 1 | |

1.1.3. 4-(N-Phenyl-N-methylamino)aniline 1.1.3.1. 2,6-Diethyl-4-(N-phenyl-N-methylamino)aniline (A) With stirring and under a weak stream of nitrogen, 6.3 ml of the borane/dimethyl sulfide complex (CH$_3$)$_2$S.BH$_3$ are added dropwise at 0° C. to a solution of 7.3 g of 2,6-diethyl-4-(N-phenyl-N-formylamino)aniline in 30 ml of tetrahydrofuran. The reaction mixture is stirred for 3 hours under reflux, then cooled to 0° C. After the dropwise addition of 30 ml of methanol, the reaction mixture is evaporated to dryness. The residue is taken up in 80 ml of toluene and 30 ml of water and the organic phase is separated and dried over sodium sulfate and silica gel. After evaporation of the solvent under vacuum, the title compound of formula

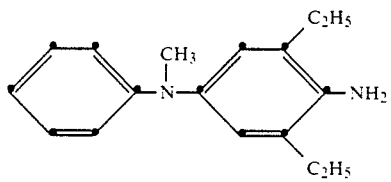

(compound 1.1.3.1.)

is obtained as a brown oil with refractive index n$_D^{25}$ = 1.5908.

1.1.3.2. 2,6-Diisopropyl-4-(N-phenyl-N-methylamino)aniline (B) 10.4 g of 2,6-diisopropyl-4-(N-phenyl-N-formylamino)aniline are dissolved in 100 ml of tetrahydrofuran and hydrogenated for 20 hours in an autoclave in the presence of 0.7 g of Re$_2$O$_7$ at 245° C. and 150 bar. The cooled reaction mixture is filtered over kieselguhr and the filtrate is concentrated by evaporation. The oily residue is taken up in a 98:2 mixture of hexane/ethyl acetate and the solution is chromatographed over silica gel. After evaporation of the solvent, the title compound of formula

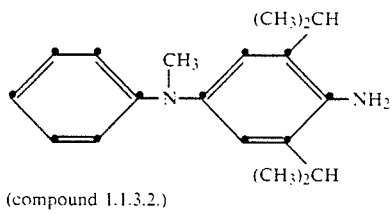

(compound 1.1.3.2.)

is obtained as a light brown oil with refractive index n$_D^{25}$ = 1.5865.

The following compounds can be prepared in a manner corresponding to that of method (A) or (B):

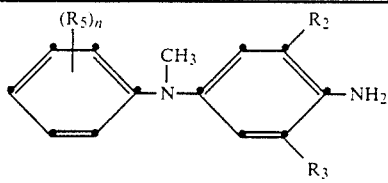

| Compound | R$_2$ | R$_3$ | R$_5$ | n | Phys. data |
|---|---|---|---|---|---|
| 1.1.3.3 | CH(CH$_3$)$_2$ | CH(CH$_3$)$_2$ | 4-Cl | 1 | m.p. 91-92° C. |
| 1.1.3.4 | CH(CH$_3$)$_2$ | CH(CH$_3$)$_2$ | 4-F | 1 | yellow oil |
| | CH$_3$ | CH$_3$ | — | 0 | |
| | CH$_3$ | C$_2$H$_5$ | — | 0 | |
| | C$_2$H$_5$ | CH(CH$_3$)$_2$ | — | 0 | |
| | C$_2$H$_5$ | CH(CH$_3$)C$_2$H$_5$ | — | 0 | |
| | C$_2$H$_5$ | CH(CH$_3$)C$_2$H$_5$ | — | 0 | |
| | CH$_3$ | CH(CH$_3$)$_2$ | — | 0 | |
| | C$_2$H$_5$ | cyclopentyl | — | 0 | |
| | C$_2$H$_5$ | cyclohexyl | — | 0 | |
| | CH(CH$_3$)$_2$ | CH(CH$_3$)$_2$ | 4-OCF$_3$ | 1 | |
| | C$_2$H$_5$ | C$_2$H$_5$ | 4-Cl | 1 | |
| | C$_2$H$_5$ | C$_2$H$_5$ | 4-OCH$_3$ | 1 | |
| | C$_2$H$_5$ | C$_2$H$_5$ | 4-F | 1 | |
| | C$_2$H$_5$ | C$_2$H$_5$ | 4-O(CH$_2$)$_3$CH$_3$ | 1 | |
| | C$_2$H$_5$ | C$_2$H$_5$ | 4-CH(CH$_3$)$_2$ | 1 | |
| | C$_2$H$_5$ | C$_2$H$_5$ | 3-Cl | 1 | |
| | C$_2$H$_5$ | C$_2$H$_5$ | 3,4-Cl$_2$ | 2 | |
| | C$_2$H$_5$ | C$_2$H$_5$ | 3,4-(CH$_3$)$_2$ | 2 | |

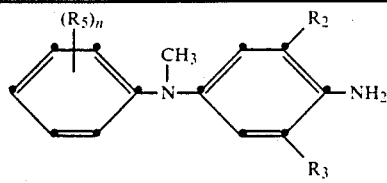

| Compound | R₂ | R₃ | R₅ | n | Phys. data |
|---|---|---|---|---|---|
|  | CH(CH₃)₂ | cyclopentyl | — | 0 |  |

1.1.4. Arylaminophenylisothiocyanates 1.1.4.1. 2,6-Diethyl-4-(N-formylanilino)phenylisothiocyanate With stirring, a solution of 24.0 g of 2,6-diethyl-4-(N-phenyl-N-formylamino)aniline in 80 ml of dichloromethane are added dropwise at 0° to 10° C. to 13.4 g of thiophosgene, 100 ml of dichloromethane, 60 ml of water and 19 g of calcium carbonate. The reaction mixture is stirred for 2 hours at room temperature and then filtered. The organic phase is separated, washed with 50 ml of water, dried over sodium sulfate and then concentrated by evaporation. The title compound of formula

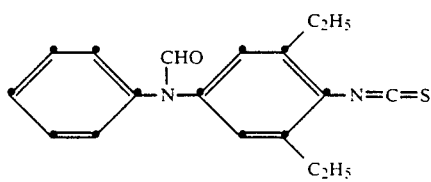

(compound 1.1.4.1.)

is obtained in the form of a crystalline powder which melts at 77°–78° C.

The following compounds are obtained in corresponding manner:

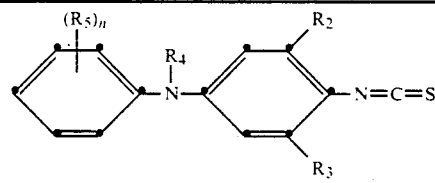

| Compound | R₂ | R₃ | R₄ | R₅ | n | Phys. data |
|---|---|---|---|---|---|---|
| 1.1.4.2. | CH(CH₃)₂ | CH(CH₃)₂ | CHO | — | 0 | m.p. 113–115° C. |
| 1.1.4.3. | C₂H₅ | CH(CH₃)C₂H₅ | CHO | — | 0 | m.p. 48–50° C. |
| 1.1.4.4. | C₂H₅ | C₂H₅ | H | — | 0 | m.p. 52–54° C. |
| 1.1.4.5. | CH(CH₃)₂ | CH(CH₃)₂ | CH₃ | — | 0 | $n_D^{25}$: 1.6375 |
| 1.1.4.6. | CH₃ | CH₃ | H | — | 0 | m.p. 80–82° C. |
| 1.1.4.7. | CH(CH₃)₂ | CH(CH₃)₂ | H | — | 0 | m.p. 87–89° C. |
| 1.1.4.8. | C₂H₅ | C₂H₅ | CHO | 4-Cl | 1 | m.p. 100–102° C. |
| 1.1.4.9. | C₂H₅ | cyclopentyl | CHO | — | 0 | m.p. 110–110.5° C. |
| 1.1.4.10. | CH(CH₃)₂ | CH(CH₃)₂ | CHO | 4-Cl | 1 | m.p. 151–153° C. |
| 1.1.4.11. | CH(CH₃)₂ | cyclopentyl | CHO | — | 0 | m.p. 110–110.5° C. |
| 1.1.4.12. | CH(CH₃)₂ | CH(CH₃)₂ | CHO | 4-F | 1 | m.p. 149–151° C. |
| 1.1.4.13. | CH(CH₃)₂ | CH(CH₃)₂ | CH₃ | 4-F | 1 | m.p. 53–55° C. |
| 1.1.4.14. | CH(CH₃)₂ | CH(CH₃)₂ | CH₃ | 4-Cl | 1 | oil |
| 1.1.4.15. | CH(CH₃)₂ | CH(CH₃)₂ | CHO | 4-C(CH₃)₃ | 1 | m.p. 115–117° C. |
| 1.1.4.16. | C₂H₅ | C₂H₅ | CHO | 4-CH₃ | 1 | m.p. 84–85° C. |
| 1.1.4.17. | C₂H₅ | CH(CH₃)₂ | CHO | 4-Cl | 1 | m.p. 95–97° C. |
| 1.1.4.18. | CH(CH₃)₂ | CH(CH₃)₂ | CHO | 3,4-Cl₂ | 2 | m.p. 139–141° C. |
| 1.1.4.19. | CH(CH₃)₂ | CH(CH₃)₂ | CHO | 4-OCH₃ | 1 | m.p. 82–84° C. |
| 1.1.4.20. | C₂H₅ | CH(CH₃)₂ | CHO | — | 0 | m.p. 73–74° C. |
| 1.1.4.21. | CH(CH₃)₂ | CH(CH₃)₂ | CHO | 4-CH₃ | 1 | m.p. 93–95° C. |
| 1.1.4.22. | CH(CH₃)₂ | CH(CH₃)₂ | CHO | 3-F | 1 | m.p. 95–96° C. |
| 1.1.4.23. | CH(CH₃)₂ | CH(CH₃)₂ | CHO | 2-F | 1 | m.p. 66–67° C. |
| 1.1.4.24. | CH(CH₃)₂ | CH(CH₃)₂ | CHO | 3-Cl | 1 | m.p. 101–103° C. |
| 1.1.4.25. | CH(CH₃)₂ | CH(CH₃)₂ | CHO | 4-CF₃ | 1 | m.p. 126–128° C. |
| 1.1.4.26. | CH(CH₃)₂ | CH(CH₃)₂ | CHO | 2,4,6-(CH₃)₃ | 3 | m.p. 70–74° C. |
| 1.1.4.27. | CH(CH₃)₂ | CH(CH₃)₂ | CHO | 2,3-(CH=CH)₂ | 2 | dark resin |
|  | CH₃ | C₂H₅ | CHO | — | 0 |  |
|  | CH₃ | C₂H₅ | H | — | 0 |  |
|  | C₂H₅ | CH(CH₃)C₂H₅ | CHO | — | 0 |  |
|  | C₂H₅ | CH(CH₃)C₂H₅ | H | — | 0 |  |
|  | CH(CH₃)₂ | CH(CH₃)₂ | CHO | — | 0 |  |
|  | C₂H₅ | C₂H₅ | CHO | — | 0 |  |
|  | C₂H₅ | C₂H₅ | H | — | 0 |  |
|  | CH₃ | CH(CH₃)₂ | CHO | — | 0 |  |
|  | C₂H₅ | cyclohexyl | CHO | — | 0 |  |
|  | CH(CH₃)₂ | CH(CH₃)₂ | CHO | 4-OCF₃ | 1 |  |
|  | C₂H₅ | C₂H₅ | CHO | 4-OCH₃ | 1 |  |
|  | C₂H₅ | C₂H₅ | CHO | 4-F | 1 |  |
|  | C₂H₅ | C₂H₅ | CHO | 4-O(CH₂)₃CH₃ | 1 |  |

-continued

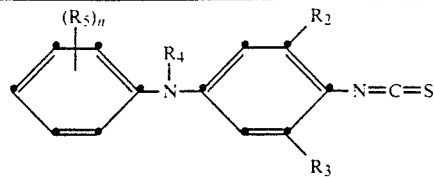

| Compound | R₂ | R₃ | R₄ | R₅ | n | Phys. data |
|---|---|---|---|---|---|---|
| | $C_2H_5$ | $C_2H_5$ | CHO | 4-CH(CH₃)₂ | 1 | |
| | $C_2H_5$ | $C_2H_5$ | CHO | 3-Cl | 1 | |
| | $C_2H_5$ | $C_2H_5$ | CHO | 3,4-Cl₂ | 2 | |
| | $C_2H_5$ | $C_2H_5$ | CHO | 3,4-(CH₃)₂ | 2 | |

1.2. Final products
1.2.1. Arylaminophenylthioureas
1.2.1.1. N-[2,6-Diethyl-4-(N-formylanilino)phenyl]-N-tert-butylthiourea With stirring, 3.7 g of tert-butylamine are added dropwise at 50° C. to a solution of 14.0 g of 2,6-diethyl-4-(N-formylanilin)phenylisothiocyanate in 30 ml of toluene and 100 ml of hexane. The reaction mixture is stirred for 2 hours at 60° C. The precipitate is then isolated by filtration, washed with hexane and dried, affording the title compound of formula

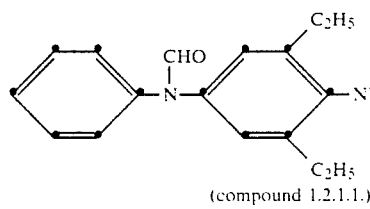

(compound 1.2.1.1.)

as a pale beige coloured powder which melts at 160°–162° C.

The following compounds are prepared in corresponding manner:

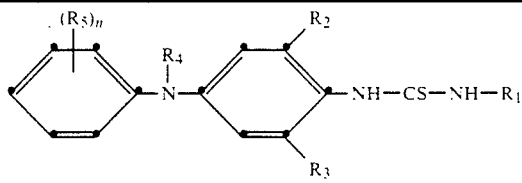

| Compound | R₁ | R₂ | R₃ | R₄ | R₅ | n | Phys. data |
|---|---|---|---|---|---|---|---|
| 1.2.1.2. | CH(CH₃)₂ | C₂H₅ | C₂H₅ | CHO | — | 0 | m.p. 180–182° C. |
| 1.2.1.3. | C(CH₃)₃ | CH(CH₃)₂ | CH(CH₃)₂ | CHO | — | 0 | m.p. 192° C./dec. |
| 1.2.1.4. | CH(CH₃)₂ | C₂H₅ | CH(CH₃)C₂H₅ | CHO | — | 0 | m.p. 156–158° C. |
| 1.2.1.5. | CH(CH₃)₂ | C₂H₅ | CH(CH₃)C₂H₅ | CHO | — | 0 | m.p. 166–168° C. |
| 1.2.1.6. | cyclopentyl | C₂H₅ | CH(CH₃)C₂H₅ | CHO | — | 0 | m.p. 159–162° C. |
| 1.2.1.7. | C(CH₃)₃ | CH(CH₃)₂ | CH(CH₃)₂ | H | — | 0 | m.p. 160° C./dec. |
| 1.2.1.8. | C(CH₃)₃ | C₂H₅ | C₂H₅ | H | — | 0 | m.p. 152° C./dec. |
| 1.2.1.9. | C(CH₃)₃ | CH(CH₃)₂ | CH(CH₃)₂ | CH₃ | — | 0 | m.p. 123–125° C. |
| 1.2.1.10. | C(CH₃)₃ | CH₃ | C₂H₅ | CHO | — | 0 | m.p. 139–141° C. |
| 1.2.1.11. | CH(CH₃)₂ | CH₃ | C₂H₅ | CHO | — | 0 | m.p. 171–173° C. |
| 1.2.1.12. | cyclopentyl | CH₃ | C₂H₅ | CHO | — | 0 | m.p. 164–166° C. |
| 1.2.1.13. | C(CH₃)₃ | C₂H₅ | C₂H₅ | CHO | 4-CH₃ | 1 | m.p. 144° C./dec. |
| 1.2.1.14. | C(CH₃)₃ | C₂H₅ | C₂H₅ | CHO | 4-Cl | 1 | m.p. 147° C./dec. |
| 1.2.1.15. | CH(CH₃)₂ | CH₃ | CH₃ | H | — | 0 | m.p. 175° C./dec. |
| 1.2.1.16. | C₁₂H₂₅ | CH(CH₃)₂ | CH(CH₃)₂ | CHO | — | 0 | m.p. 144–146° C. |
| 1.2.1.17. | CH(CH₃)₂ | CH(CH₃)₂ | CH(CH₃)₂ | CHO | — | 0 | m.p. 207–209° C. |
| 1.2.1.18. | CH(CH₃)CH₂OCH₃ | CH(CH₃)₂ | CH(CH₃)₂ | CHO | — | 0 | m.p. 204–205° C. |
| 1.2.1.19. | CH(CH₃)C₂H₅ | CH(CH₃)₂ | CH(CH₃)₂ | CHO | — | 0 | m.p. 203–205° C. |
| 1.2.1.20. | C(CH₃)₃ | CH(CH₃)₂ | cyclopentyl | CHO | — | 0 | m.p. 189.5–190.5° C. |
| 1.2.1.21. | C(CH₃)₂C₂H₅ | CH(CH₃)₂ | cyclopentyl | CHO | — | 0 | m.p. 190–191° C. |
| 1.2.1.22. | C(CH₃)₃ | CH(CH₃)₂ | CH(CH₃)₂ | CHO | 4-CH₃ | 1 | m.p. 173° C./dec. |
| 1.2.1.23. | C(CH₃)₃ | CH(CH₃)₂ | CH(CH₃)₂ | CHO | 4-CF₃ | 1 | m.p. 155° C./dec. |
| 1.2.1.24. | CH(CH₃)₂ | CH(CH₃)₂ | CH(CH₃)₂ | CH₃ | — | 0 | m.p. 112–115° C. |
| 1.2.1.25. | cyclopentyl | CH(CH₃)₂ | CH(CH₃)₂ | CHO | — | 0 | m.p. 210° C./dec. |
| 1.2.1.26. | C(CH₃)₃ | CH(CH₃)₂ | CH(CH₃)₂ | CHO | 3-F | 1 | m.p. 203° C./dec. |
| 1.2.1.27. | C(CH₃)₃ | CH(CH₃)₂ | CH(CH₃)₂ | CHO | 2-F | 1 | m.p. 199° C./dec. |
| 1.2.1.28. | C(CH₃)₃ | CH(CH₃)₂ | CH(CH₃)₂ | CHO | 2,3-—CH=CH— | 2 | m.p. 165° C./dec. |
| 1.2.1.29. | C(CH₃)₃ | CH(CH₃)₂ | CH(CH₃)₂ | CHO | 4-Cl | 1 | m.p. 167° C./dec. |
| 1.2.1.30. | cyclopentyl | CH(CH₃)₂ | CH(CH₃)₂ | CHO | — | 0 | m.p. 210° C./dec. |
| 1.2.1.31. | C(CH₃)₃ | CH₃ | CH(CH₃)₂ | CH₃ | 4-Cl | 1 | m.p. 150° C./dec. |
| 1.2.1.32. | C(CH₃)₃ | CH(CH₃)₂ | CH(CH₃)₂ | CHO | 4-F | 1 | m.p. 150–151° C. |
| 1.2.1.33. | C(CH₃)₃ | C₂H₅ | CH(CH₃)₂ | CHO | 4-Cl | 1 | m.p. 152° C./dec. |
| 1.2.1.34. | C(CH₃)₃ | CH(CH₃)₂ | CH(CH₃)₂ | CH₃ | 4-F | 1 | m.p. 145° C./dec. |
| 1.2.1.35. | CH(CH₃)₂ | CH(CH₃)₂ | CH(CH₃)₂ | CHO | 4-F | 1 | m.p. 207° C./dec. |
| 1.2.1.36. | C(CH₃)₂C₂H₅ | CH(CH₃)₂ | CH(CH₃)₂ | CHO | — | 0 | m.p. 189° C./dec. |
| 1.2.1.37. | CH(C₂H₅)₂ | CH(CH₃)₂ | CH(CH₃)₂ | CHO | — | 0 | m.p. 207–210° C. |

-continued

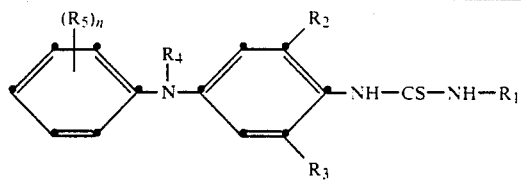

| Compound | R₁ | R₂ | R₃ | R₄ | R₅ | n | Phys.data |
|---|---|---|---|---|---|---|---|
| 1.2.1.38. | CH(CH₃)CH(CH₃)₂ | CH(CH₃)₂ | CH(CH₃)₂ | CHO | — | 0 | m.p. 210–212° C. |
| 1.2.1.39. | CH(CH₃)₂ | CH(CH₃)₂ | CH(CH₃)₂ | CH₃ | 4-F | 1 | m.p. 146–148° C. |
| 1.2.1.40. | C(CH₃)₃ | CH(CH₃)₂ | CH(CH₃)₂ | CHO | 3,4-Cl₂ | 2 | m.p. 159° C./dec. |
| 1.2.1.41. | C(CH₃)₃ | CH(CH₃)₂ | CH(CH₃)₂ | CHO | 4-OCH₃ | 1 | m.p. 168° C./dec. |
| 1.2.1.42. | C(CH₃)₃ | C₂H₅ | CH(CH₃)₂ | CHO | — | 0 | m.p. 177° C./dec. |
| 1.2.1.43. | CH(CH₃)(CH₂)₂CH₃ | CH(CH₃)₂ | CH(CH₃)₂ | CHO | — | 0 | m.p. 188–190° C. |
| 1.2.1.44. | CH(CH₃)₂ | C₂H₅ | CH(CH₃)₂ | CHO | 4-Cl | 1 | m.p. 181–183° C. |
| 1.2.1.45. | C(CH₃)₃ | CH(CH₃)₂ | CH(CH₃)₂ | CHO | 4-C(CH₃)₃ | 1 | m.p. 170° C./dec. |
| 1.2.1.46. | CH(CH₃)₂ | CH(CH₃)₂ | CH(CH₃)₂ | CHO | 4-C(CH₃)₃ | 1 | m.p. 208° C./dec. |
| | C(CH₃)₃ | CH₃ | CH₃ | CHO | — | 0 | |
| | CH(CH₃)₂ | CH₃ | CH₃ | CHO | — | 0 | |
| | CH(CH₃)C₂H₅ | C₂H₅ | C₂H₅ | CHO | — | 0 | |
| | CH(CH₃)CH₂OCH₃ | C₂H₅ | C₂H₅ | CHO | — | 0 | |
| | cyclopropyl | C₂H₅ | C₂H₅ | CHO | — | 0 | |
| | C(CH₃)₃ | C₂H₅ | cyclopentyl | CHO | — | 0 | |
| | CH₃ | CH(CH₃)₂ | CH(CH₃)₂ | CHO | — | 0 | |
| | cyclohexyl | CH(CH₃)₂ | CH(CH₃)₂ | CHO | — | 0 | |
| | cyclooctyl | CH(CH₃)₂ | CH(CH₃)₂ | CHO | — | 0 | |
| | —CH(CH₃)-cyclohexyl | CH(CH₃)₂ | CH(CH₃)₂ | CHO | — | 0 | |
| | 2,6-diethyl-cyclohexyl | CH(CH₃)₂ | CH(CH₃)₂ | CHO | — | 0 | |
| | CH[CH(CH₃)₂]₂ | CH(CH₃)₂ | CH(CH₃)₂ | CHO | — | 0 | |
| | CH(CH₃)CH(CH₃)₂ | CH(CH₃)₂ | CH(CH₃)₂ | CHO | — | 0 | |
| | CH(CH₃)₂ | CH(CH₃)₂ | cyclopentyl | CHO | — | 0 | |
| | C(CH₃)₃ | CH(CH₃)₂ | CH(CH₃)₂ | CHO | 2,4,6-(CH₃)₃ | 3 | |
| | C(CH₃)₃ | CH(CH₃)₂ | CH(CH₃)₂ | CHO | 3-Cl | | |
| | cyclopropyl | CH(CH₃)₂ | CH(CH₃)₂ | CHO | — | 0 | |
| | CH(CH₃)₂ | C₂H₅ | C₂H₅ | CHO | 4-CH₃ | 1 | |
| | CH(CH₃)₂ | C₂H₅ | C₂H₅ | CHO | 4-Cl | 1 | |
| | C(CH₃)₃ | C₂H₅ | C₂H₅ | CHO | 4-OCH₃ | 1 | |
| | C(CH₃)₃ | C₂H₅ | C₂H₅ | CHO | 4-F | 1 | |
| | C(CH₃)₃ | C₂H₅ | C₂H₅ | CHO | 2,4,6-(CH₃)₃ | 3 | |
| | C(CH₃)₃ | C₂H₅ | C₂H₅ | CHO | 4-CH(CH₃)₂ | 1 | |
| | CH(CH₃)₂ | CH(CH₃)₂ | CH(CH₃)₂ | CHO | 4-CH₃ | 1 | |
| | C(CH₃)₃ | CH(CH₃)₂ | CH(CH₃)₂ | CHO | 4-OCHF₃ | 1 | |
| | C(CH₃)₃ | C₂H₅ | C₂H₅ | CHO | 3,4-(CH₂)₃ | 1 | |
| | C(CH₃)₃ | C₂H₅ | C₂H₅ | CHO | 3,4-(CH₂=CH)₂ | 2 | |
| | C(CH₃)₃ | C₂H₅ | C₂H₅ | CH₃ | — | 0 | |
| | CH(CH₃)₂ | C₂H₅ | C₂H₅ | CH₃ | — | 0 | |

1.2.2. Arylaminophenylisothioureas 1.2.2.1. N-[2,6-Diethyl-4-(N-formylanilino)phenyl]-N'-tert-butyl-S-methylisothiourea 2.6 g of methyl iodide are added at room temperature to 5.2 g N-[2,6-diethyl-4-(N-formylanilino)phenyl]-N'-tert-butylthiourea in 50 ml ethanol and the mixture is stirred for 2 hours under gentle reflux. The solvent is then removed by evaporation and the residue is taken up in 50 ml of dichloromethane and 40 ml of a 10% aqueous solution of sodium carbonate. The organic phase is separated, dried over sodium sulfate and dried on a rotary evaporator. The residue is recrystallised from toluene. The title compound of formula

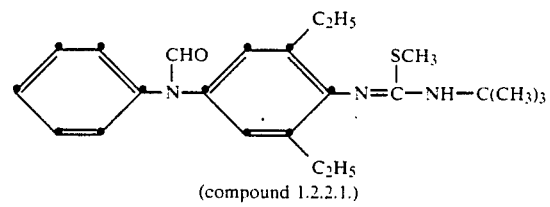

(compound 1.2.2.1.)

is obtained as a white powder which melts at 168°–170° C.

The following compounds are prepared in corresponding manner:

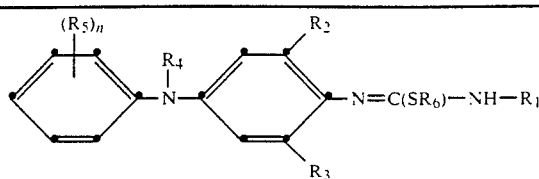

| Compound | R₁ | R₂ | R₃ | R₄ | R₅ | n | R₆ | Phys. data |
|---|---|---|---|---|---|---|---|---|
| 1.2.2.2. | C(CH₃)₃ | C₂H₅ | CH(CH₃)C₂H₅ | CHO | — | 0 | C₂H₅ | m.p. 108–110° C. |
| 1.2.2.3. | C(CH₃)₃ | CH₃ | CH₃ | H | — | 0 | CH₃ | m.p. 101–103° C. |
| 1.2.2.4. | C(CH₃)₃ | C₂H₅ | C₂H₅ | CHO | 4-CH₃ | 1 | CH₃ | m.p. 179–181° C. |
| 1.2.2.5. | C(CH₃)₃ | CH(CH₃)₂ | cyclopentyl | CHO | — | 0 | CH₃ | m.p. 150.5–151° C. |
| 1.2.2.6. | C(CH₃)₃ | CH(CH₃)₂ | CH(CH₃)₂ | CH₃ | 4-Cl | 1 | CH₃ | m.p. 122–123° C. |
| 1.2.2.7. | C(CH₃)₃ | CH(CH₃)₂ | CH(CH₃)₂ | CH₃ | 4-F | 1 | CH₃ | m.p. 101–103° C. |
| 1.2.2.8. | C(CH₃)₃ | CH(CH₃)₂ | CH(CH₃)₂ | CH₃ | 4-F | 1 | C₂H₅ | m.p. 93–94° C. |
| 1.2.2.9. | CH(CH₃)₂ | C₂H₅ | CH(CH₃)C₂H₅ | H | — | 0 | (CH₂)₂CH₃ | $n_D^{30}$: 1.5774 |
| 1.2.2.10. | C(CH₃)₃ | CH₃ | C₂H₅ | H | — | 0 | CH₃ | m.p. 101–103° C. |
| 1.2.2.11. | C(CH₃)₂C₂H₅ | CH(CH₃)₂ | cyclopentyl | CHO | — | 0 | CH₃ | m.p. 134–135.5° C. |
| 1.2.2.12. | C(CH₃)₃ | CH(CH₃)₂ | CH(CH₃)₂ | CH₃ | 4-F | 1 | Allyl | $n_D^{21}$: 1.571 |
|  | CH(CH₃)₂ | C₂H₅ | C₂H₅ | CHO | — | 0 | CH₃ |  |
|  | C(CH₃)₃ | CH(CH₃)₂ | CH(CH₃)₂ | CHO | — | 0 | C₂H₅ |  |
|  | CH(CH₃)₂ | C₂H₅ | CH(CH₃)C₂H₅ | CHO | — | 0 | CH₃ |  |
|  | C(CH₃)₃ | C₂H₅ | CH(CH₃)C₂H₅ | CHO | — | 0 | CH₃ |  |
|  | cyclopentyl | C₂H₅ | CH(CH₃)C₂H₅ | CHO | — | 0 | CH₃ |  |
|  | C(CH₃)₃ | CH(CH₃)₂ | CH(CH₃)₂ | H | — | 0 | CH₃ |  |
|  | C(CH₃)₃ | C₂H₅ | C₂H₅ | H | — | 0 | C₂H₅ |  |
|  | C(CH₃)₃ | CH(CH₃)₂ | CH(CH₃)₂ | CH₃ | — | 0 | C₂H₅ |  |
|  | CH(CH₃)₂ | CH₃ | CH₃ | CHO | — | 0 | CH₃ |  |
|  | C(CH₃)₃ | CH₃ | C₂H₅ | CHO | — | 0 | CH₃ |  |
|  | CH(CH₃)₂ | CH₃ | C₂H₅ | CHO | — | 0 | CH₃ |  |
|  | cyclopentyl | CH₃ | C₂H₅ | CHO | — | 0 | CH₃ |  |
|  | CH(CH₃)C₂H₅ | C₂H₅ | C₂H₅ | CHO | — | 0 | C₂H₅ |  |
|  | CH(CH₃)CH₂OCH₃ | C₂H₅ | C₂H₅ | CHO | — | 0 | C₂H₅ |  |
|  | cyclopropyl | C₂H₅ | C₂H₅ | CHO | — | 0 | C₂H₅ |  |
|  | C(CH₃)₃ | C₂H₅ | cyclopentyl | CHO | — | 0 | CH₃ |  |
|  | CH₃ | CH(CH₃)₂ | CH(CH₃)₂ | CHO | — | 0 | C₂H₅ |  |
|  | cyclohexyl | CH(CH₃)₂ | CH(CH₃)₂ | CHO | — | 0 | CH₃ |  |
|  | cyclooctyl | CH(CH₃)₂ | CH(CH₃)₂ | CHO | — | 0 | CH₃ |  |
|  | C₁₂H₂₅ | CH(CH₃)₂ | CH(CH₃)₂ | CHO | — | 0 | C₂H₅ |  |
|  | —CH(CH₃)-cyclohexyl | CH(CH₃)₂ | CH(CH₃)₂ | CHO | — | 0 | C₂H₅ |  |
|  | 2,6-diethylcyclohexyl | CH(CH₃)₂ | CH(CH₃)₂ | CHO | — | 0 | C₂H₅ |  |
|  | CH[CH(CH₃)₂]₂ | CH(CH₃)₂ | CH(CH₃)₂ | CHO | — | 0 | CH₃ |  |
|  | CH(CH₃)₂ | CH(CH₃)₂ | CH(CH₃)₂ | CHO | — | 0 | C₂H₅ |  |
|  | CH(CH₃)CH(CH₃)₂ | CH(CH₃)₂ | CH(CH₃)₂ | CHO | — | 0 | CH₃ |  |
|  | CH(CH₃)CH₂OCH₃ | CH(CH₃)₂ | CH(CH₃)₂ | CHO | — | 0 | C₂H₅ |  |
|  | CH(CH₃)C₂H₅ | CH(CH₃)₂ | CH(CH₃)₂ | CHO | — | 0 | C₂H₅ |  |
|  | CH(CH₃)₂ | CH(CH₃)₂ | cyclopentyl | CHO | — | 0 | CH₃ |  |
|  | cyclopropyl | CH(CH₃)₂ | CH(CH₃)₂ | CHO | — | 0 | C₂H₅ |  |
|  | CH(CH₃)₂ | C₂H₅ | C₂H₅ | CHO | 4-CH₃ | 1 | CH₃ |  |
|  | C(CH₃)₃ | C₂H₅ | C₂H₅ | CHO | 4-Cl | 1 | CH₃ |  |
|  | CH(CH₃)₂ | C₂H₅ | C₂H₅ | CHO | 4-Cl | 1 | CH₃ |  |
|  | C(CH₃)₃ | C₂H₅ | C₂H₅ | CHO | 4-OCH₃ | 1 | CH₃ |  |
|  | C(CH₃)₃ | C₂H₅ | C₂H₅ | CHO | 4-F | 1 | CH₃ |  |
|  | C(CH₃)₃ | C₂H₅ | C₂H₅ | CHO | 2,4,6-(CH₃)₃ | 3 | CH₃ |  |
|  | C(CH₃)₃ | C₂H₅ | C₂H₅ | CHO | 4-CH(CH₃)₂ | 1 | CH₃ |  |
|  | C(CH₃)₃ | CH(CH₃)₂ | CH(CH₃)₂ | CHO | 4-CH₃ | 1 | C₂H₅ |  |
|  | CH(CH₃)₂ | CH(CH₃)₂ | CH(CH₃)₂ | CHO | 4-CH₃ | 1 | C₂H₅ |  |
|  | C(CH₃)₃ | CH(CH₃)₂ | CH(CH₃)₂ | CHO | 4-OCF₃ | 1 | CH₃ |  |
|  | C(CH₃)₃ | CH(CH₃)₂ | CH(CH₃)₂ | CHO | 4-CF₃ | 1 | CH₃ |  |
|  | C(CH₃)₃ | C₂H₅ | C₂H₅ | CHO | 3,4-(CH₂)₄- | 2 | CH₃ |  |
|  | C(CH₃)₃ | C₂H₅ | C₂H₅ | CHO | 3,4-(CH₂=CH)₂- | 2 | CH₃ |  |
|  | C(CH₃)₃ | C₂H₅ | C₂H₅ | CH₃ | — | 0 | CH₃ |  |
|  | CH(CH₃)₂ | C₂H₅ | C₂H₅ | CH₃ | — | 0 | CH₃ |  |
|  | CH(CH₃)₂ | CH(CH₃)₂ | CH(CH₃)₂ | CH₃ | — | 0 | CH₃ |  |
|  | CH(CH₃)₂ | CH(CH₃)₂ | CH(CH₃)₂ | CHO | — | 0 | C₃H₇ |  |
|  | C(CH₃)₃ | CH(CH₃)₂ | CH(CH₃)₂ | CHO | — | 0 | C₄H₉ |  |
|  | C(CH₃)₃ | CH(CH₃)₂ | CH(CH₃)₂ | CHO | — | 0 | allyl |  |

1.2.3. Arylaminophenylcarbodiimides 1.2.3.1. N-[2,6-Diethyl-4-(N-formylanilino)phenyl]-N'-tert-butylcarbodiimide With stirring, 3.2 g of triethylamine are added dropwise at room temperature to 6.0 g of N-[2,6-diethyl-4-(N-formylanilino)phenyl]-N'-tert-butylthiourea and 4.8 g of 2-chloro-1-methylpyridinium iodide in 30 ml of acetonitrile. The reaction mixture is stirred for 1 hour at 70° C. and then concentrated by evaporation at 50° C. on a rotary evaporator. The residue is taken up in 50 ml of hexane and 30 ml of cold water. The hexane phase is separated, washed with water, dried over sodium sulfate and concentrated by evaporation, to give the title compound of formula

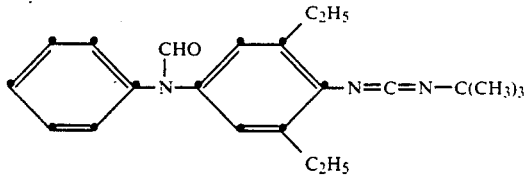

-continued
(compound 1.2.3.1.)

as a yellowish oil with refractive index $n_D^{25}$: 1.5840.
The following compounds are prepared in corresponding manner:

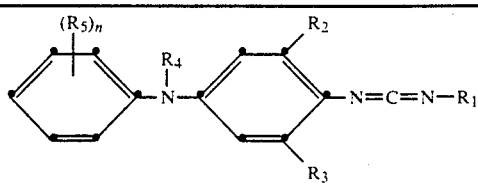

| Compound | $R_1$ | $R_2$ | $R_3$ | $R_4$ | $R_5$ | n | Phys. data |
|---|---|---|---|---|---|---|---|
| 1.2.3.2. | CH(CH$_3$)$_2$ | C$_2$H$_5$ | C$_2$H$_5$ | CHO | — | 0 | $n_D^{25}$: 1.5905 |
| 1.2.3.3. | C(CH$_3$)$_3$ | CH(CH$_3$)$_2$ | CH(CH$_3$)$_2$ | CHO | — | 0 | m.p. 88–90° C. |
| 1.2.3.4. | C(CH$_3$)$_3$ | C$_2$H$_5$ | CH(CH$_3$)C$_2$H$_5$ | CHO | — | 0 | $n_D^{25}$: 1.5726 |
| 1.2.3.5. | CH(CH$_3$)$_2$ | C$_2$H$_5$ | CH(CH$_3$)C$_2$H$_5$ | CHO | — | 0 | $n_D^{25}$: 1.5790 |
| 1.2.3.6. | cyclopentyl | C$_2$H$_5$ | CH(CH$_3$)C$_2$H$_5$ | CHO | — | 0 | $n_D^{25}$: 1.5894 |
| 1.2.3.7. | C(CH$_3$)$_3$ | C$_2$H$_5$ | CH(CH$_3$)C$_2$H$_5$ | CHO | — | 0 | $n_D^{25}$: 1.5726 |
| 1.2.3.8. | CH(CH$_3$)$_2$ | C$_2$H$_5$ | CH(CH$_3$)C$_2$H$_5$ | CHO | — | 0 | $n_D^{25}$: 1.5790 |
| 1.2.3.9. | cyclopentyl | C$_2$H$_5$ | CH(CH$_3$)C$_2$H$_5$ | CHO | — | 0 | $n_D^{25}$: 1.5894 |
| 1.2.3.10. | C(CH$_3$)$_3$ | CH(CH$_3$)$_2$ | CH(CH$_3$)$_2$ | CH$_3$ | — | 0 | $n_D^{25}$: 1.5780 |
| 1.2.3.11. | C(CH$_3$)$_3$ | CH$_3$ | C$_2$H$_5$ | CHO | — | 0 | $n_D^{25}$: 1.5881 |
| 1.2.3.12. | CH(CH$_3$)$_2$ | CH$_3$ | C$_2$H$_5$ | CHO | — | 0 | $n_D^{30}$: 1.5955 |
| 1.2.3.13. | cyclopentyl | CH$_3$ | C$_2$H$_5$ | CHO | — | 0 | $n_D^{25}$: 1.6045 |
| 1.2.3.14. | C(CH$_3$)$_3$ | C$_2$H$_5$ | C$_2$H$_5$ | CHO | 4-CH$_3$ | 1 | $n_D^{24}$: 1.5829 |
| 1.2.3.15. | C(CH$_3$)$_3$ | C$_2$H$_5$ | C$_2$H$_5$ | CHO | 4-Cl | 1 | $n_D^{24}$: 1.584 |
| 1.2.3.16. | C$_{12}$H$_{25}$ | CH(CH$_3$)$_2$ | CH(CH$_3$)$_2$ | CHO | — | 0 | $n_D^{25}$: 1.5480 |
| 1.2.3.17. | CH(CH$_3$)$_2$ | CH(CH$_3$)$_2$ | CH(CH$_3$)$_2$ | CHO | — | 0 | m.p. 51–53° C. |
| 1.2.3.18. | CH(CH$_3$)CH(CH$_3$)$_2$ | CH(CH$_3$)$_2$ | CH(CH$_3$)$_2$ | CHO | — | 0 | $n_D^{25}$: 1.5769 |
| 1.2.3.19. | CH(CH$_3$)CH$_2$OCH$_3$ | CH(CH$_3$)$_2$ | CH(CH$_3$)$_2$ | CHO | — | 0 | $n_D^{25}$: 1.5730 |
| 1.2.3.20. | CH(CH$_3$)C$_2$H$_5$ | CH(CH$_3$)$_2$ | CH(CH$_3$)$_2$ | CHO | — | 0 | $n_D^{25}$: 1.5737 |
| 1.2.3.21. | C(CH$_3$)$_3$ | CH(CH$_3$)$_2$ | cyclopentyl | CHO | — | 0 | m.p. 107–109° C. |
| 1.2.3.22. | C(CH$_3$)$_3$ | CH(CH$_3$)$_2$ | CH(CH$_3$)$_2$ | CHO | 4-CH$_3$ | 1 | $n_D^{25}$: 1.5636 |
| 1.2.3.23. | C(CH$_3$)$_3$ | CH(CH$_3$)$_2$ | CH(CH$_3$)$_2$ | CHO | 4-CF$_3$ | 1 | $n_D^{40}$: 1.5373 |
| 1.2.3.24. | CH(CH$_3$)$_2$ | CH(CH$_3$)$_2$ | CH(CH$_3$)$_2$ | CH$_3$ | — | 0 | $n_D^{25}$: 1.5844 |
| 1.2.3.25. | CH(C$_2$H$_5$)$_2$ | CH(CH$_3$)$_2$ | CH(CH$_3$)$_2$ | CHO | — | 0 | $n_D^{25}$: 1.5703 |
| 1.2.3.26. | C(CH$_3$)$_3$ | CH(CH$_3$)$_2$ | CH(CH$_3$)$_2$ | H | — | 0 | $n_D^{25}$: 1.6193 |
| 1.2.3.27. | cyclopentyl | CH(CH$_3$)$_2$ | CH(CH$_3$)$_2$ | CHO | — | 0 | m.p. 67–69° C. |
| 1.2.3.28. | C(CH$_3$)$_3$ | CH(CH$_3$)$_2$ | CH(CH$_3$)$_2$ | CH$_3$ | 4-Cl | 1 | $n_D^{25}$: 1.5854 |
| 1.2.3.29. | C(CH$_3$)$_3$ | C$_2$H$_5$ | CH(CH$_3$)$_2$ | CHO | 4-Cl | 1 | $n_D^{40}$: 1.5795 |
| 1.2.3.30. | C(CH$_3$)$_3$ | CH(CH$_3$)$_2$ | CH(CH$_3$)$_2$ | CH$_3$ | 4-F | 1 | $n_D^{23}$: 1.5676 |
| 1.2.3.31. | CH(CH$_3$)(CH$_2$)$_2$CH$_3$ | CH(CH$_3$)$_2$ | CH(CH$_3$)$_2$ | CHO | — | 0 | $n_D^{25}$: 1.5691 |
| 1.2.3.32. | CH(CH$_3$)$_2$ | C$_2$H$_5$ | CH(CH$_3$)$_2$ | CHO | 4-Cl | 1 | $n_D^{25}$: 1.5896 |
| 1.2.3.33. | C(CH$_3$)$_3$ | CH(CH$_3$)$_2$ | CH(CH$_3$)$_2$ | CHO | 4-F | 1 | m.p. 76–78° C. |
| 1.2.3.34. | CH(CH$_3$)$_2$ | CH(CH$_3$)$_2$ | CH(CH$_3$)$_2$ | CHO | 4-F | 1 | $n_D^{25}$: 1.5691 |
| 1.2.3.35. | C(CH$_3$)$_3$ | CH(CH$_3$)$_2$ | CH(CH$_3$)$_2$ | CHO | 4-OCH$_3$ | 1 | m.p. 59–61 |
| 1.2.3.36. | C(CH$_3$)$_3$ | CH(CH$_3$)$_2$ | CH(CH$_3$)$_2$ | CHO | 3,4-Cl$_2$ | 2 | m.p. 104–106° C. |
| 1.2.3.37. | C(CH$_3$)$_3$ | C$_2$H$_5$ | CH(CH$_3$)$_2$ | CHO | — | 0 | m.p. 60–61° C. |
| 1.2.3.38. | C(CH$_3$)$_2$C$_2$H$_5$ | CH(CH$_3$)$_2$ | CH(CH$_3$)$_2$ | CHO | — | 0 | m.p. 73–75° C. |
| 1.2.3.39. | C(CH$_3$)$_3$ | CH(CH$_3$)$_2$ | CH(CH$_3$)$_2$ | CHO | 3-Cl | 1 | $n_D^{40}$: 1.5724 |
| 1.2.3.40. | C(CH$_3$)$_3$ | CH(CH$_3$)$_2$ | CH(CH$_3$)$_2$ | CHO | 4-C(CH$_3$)$_3$ | 1 | m.p. 109–111° C. |
| 1.2.3.41. | CH(CH$_3$)$_2$ | CH(CH$_3$)$_2$ | CH(CH$_3$)$_2$ | CHO | 4-C(CH$_3$)$_3$ | 1 | m.p. 64–67° C. |
| 1.2.3.42. | C(CH$_3$)$_2$C$_2$H$_5$ | CH(CH$_3$)$_2$ | cyclopentyl | CHO | — | 0 | m.p. 89–91° C. |
| 1.2.3.43. | C(CH$_3$)$_3$ | CH(CH$_3$)$_2$ | CH(CH$_3$)$_2$ | CHO | 3-F | 1 | m.p. 78–80° C. |
| 1.2.3.44. | C(CH$_3$)$_3$ | CH(CH$_3$)$_2$ | CH(CH$_3$)$_2$ | CHO | 2-F | 1 | $n_D^{25}$: 1.5584 |
| 1.2.3.45. | C(CH$_3$)$_3$ | CH(CH$_3$)$_2$ | CH(CH$_3$)$_2$ | CHO | 2,3-(CH=CH)$_2$ | 2 | $n_D^{21}$: 1.595 |
| 1.2.3.46. | C(CH$_3$)$_3$ | CH(CH$_3$)$_2$ | CH(CH$_3$)$_2$ | CHO | 4-Cl | 1 | $n_D^{21}$: 1.579 |
| | CH(CH$_3$)$_2$ | C$_2$H$_5$ | C$_2$H$_5$ | CHO | — | 0 | |
| | C(CH$_3$)$_3$ | CH(CH$_3$)$_2$ | CH(CH$_3$)$_2$ | CHO | — | 0 | |
| | C(CH$_3$)$_3$ | CH(CH$_3$)$_2$ | CH(CH$_3$)$_2$ | H | — | 0 | |
| | C(CH$_3$)$_3$ | C$_2$H$_5$ | C$_2$H$_5$ | H | — | 0 | |
| | C(CH$_3$)$_3$ | CH$_3$ | CH$_3$ | CHO | — | 0 | |
| | CH(CH$_3$)$_2$ | CH$_3$ | CH$_3$ | CHO | — | 0 | |
| | CH(CH$_3$)C$_2$H$_5$ | C$_2$H$_5$ | C$_2$H$_5$ | CHO | — | 0 | |
| | CH(CH$_3$)CH$_2$OCH$_3$ | C$_2$H$_5$ | C$_2$H$_5$ | CHO | — | 0 | |
| | cyclopropyl | C$_2$H$_5$ | C$_2$H$_5$ | CHO | — | 0 | |
| | C(CH$_3$)$_3$ | C$_2$H$_5$ | cyclopentyl | CHO | — | 0 | |
| | CH$_3$ | CH(CH$_3$)$_2$ | CH(CH$_3$)$_2$ | CHO | — | 0 | |
| | cyclohexyl | CH(CH$_3$)$_2$ | CH(CH$_3$)$_2$ | CHO | — | 0 | |
| | cyclooctyl | CH(CH$_3$)$_2$ | CH(CH$_3$)$_2$ | CHO | — | 0 | |
| | —CH(CH$_3$)-cyclohexyl | CH(CH$_3$)$_2$ | CH(CH$_3$)$_2$ | CHO | — | 0 | |
| | 2,6-diethylcyclohexyl | CH(CH$_3$)$_2$ | CH(CH$_3$)$_2$ | CHO | — | 0 | |
| | CH[CH(CH$_3$)$_2$]$_2$ | CH(CH$_3$)$_2$ | CH(CH$_3$)$_2$ | CHO | — | 0 | |

-continued

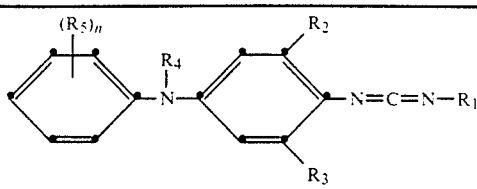

| Compound $R_1$ | $R_2$ | $R_3$ | $R_4$ | $R_5$ | n | Phys. data |
|---|---|---|---|---|---|---|
| $C(CH_3)_3$ | $CH(CH_3)_2$ | cyclopentyl | CHO | — | 0 | |
| cyclopropyl | $CH(CH_3)_2$ | $CH(CH_3)_2$ | CHO | — | 0 | |
| $CH(CH_3)_2$ | $C_2H_5$ | $C_2H_5$ | CHO | 4-$CH_3$ | 1 | |
| $CH(CH_3)_2$ | $C_2H_5$ | $C_2H_5$ | CHO | 4-Cl | 1 | |
| $C(CH_3)_3$ | $C_2H_5$ | $C_2H_5$ | CHO | 4-$OCH_3$ | 1 | |
| $C(CH_3)_3$ | $C_2H_5$ | $C_2H_5$ | CHO | 4-F | 1 | |
| $C(CH_3)_3$ | $C_2H_5$ | $C_2H_5$ | CHO | 4-$CH(CH_3)_2$ | | |
| $CH(CH_3)_2$ | $CH(CH_3)_2$ | $CH(CH_3)_2$ | CHO | 4-$CH_3$ | 1 | |
| $C(CH_3)_3$ | $CH(CH_3)_2$ | $CH(CH_3)_2$ | CHO | 4-$OCHF_2$ | 1 | |
| $C(CH_3)_3$ | $CH(CH_3)_2$ | $CH(CH_3)_2$ | CHO | 2,4,6-$(CH_3)_3$ | | |
| $C(CH_3)_3$ | $CH(CH_3)_2$ | $CH(CH_3)_2$ | CHO | 3-Cl | 1 | |
| $C(CH_3)_3$ | $C_2H_5$ | $C_2H_5$ | CHO | 3,4-$(CH_2)_3$ | 2 | |
| $C(CH_3)_3$ | $C_2H_5$ | $C_2H_5$ | CHO | 3,4-$(CH_2=CH)_2$ | 2 | |
| $C(CH_3)_3$ | $C_2H_5$ | $C_2H_5$ | $CH_3$ | — | 0 | |
| $CH(CH_3)_2$ | $C_2H_5$ | $C_2H_5$ | $CH_3$ | — | 0 | |

EXAMPLE 2

Formulations of compounds of formula I according to Preparatory Examples 1.2. (throughout, percentages are by weight)

| 2.1. Emulsifiable concentrates | (a) | (b) |
|---|---|---|
| a compound according to Preparatory Examples 1.2. | 10% | 25% |
| calcium dodecylbenzenesulfonate | — | 5% |
| castor oil polyethylene glycol ether (36 mol of ethylene oxide) | 25% | 5% |
| cyclohexanone | — | 40% |
| butanol | 15% | — |
| xylene mixture | — | 25% |
| ethyl acetate | 50% | — |

Emulsions of any required concentration can be produced from such concentrates by dilution with water.

| 2.2. Solutions | (a) | (b) |
|---|---|---|
| a compound according to Preparatory Examples 1.2. | 10% | 5% |
| polyethylene glycol 400 | 70% | — |
| N-methyl-2-pyrrolidone | 20% | 20% |
| epoxidised coconut oil | — | 1% |
| petroleum distillate (boiling range 160-190° C. | — | 74% |

These solutions are suitable for application in the form of microdrops.

| 2.3. Granulates | (a) | (b) |
|---|---|---|
| a compound according to Preparatory Examples 1.2. | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 2.4. Extruder granulate | |
|---|---|
| a compound according to Preparatory Examples 1.2. | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 2.5. Coated granulate | |
|---|---|
| a compound according to Preparatory Examples 1.2. | 3% |
| polyethylene glycol 200 | 3% |
| kaolin | 94% |

The finely ground active ingredient is uniformly applied, in a mixer, to the kaolin moistened with polyethylene glycol. Non-dusty coated granulates are obtained in this manner.

| 2.6. Dusts | (a) | (b) | (c) | (d) |
|---|---|---|---|---|
| a compound according to Preparatory Examples 1.2. | 2% | 5% | 5% | 8% |
| highly dispersed silicic acid | 1% | 5% | — | — |
| talcum | 97% | — | 95% | — |
| kaolin | — | 90% | — | 92% |

Ready-for-use dusts are obtained by intimately mixing the carriers with the active ingredient and grinding the mixture in a suitable mill.

| 2.7. Wettable powders | (a) | (b) | (c) |
|---|---|---|---|
| a compound according to Preparatory Examples 1.2. | 20% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7-8 mol of ethylene oxide) | — | 2% | — |

-continued

| 2.7. Wettable powders | (a) | (b) | (c) |
|---|---|---|---|
| highly dispersed silicic acid | 5% | 10% | 10% |
| kaolin | 67% | 27% | — |

The active ingredient is thoroughly mixed with the adjuvants and the mixture is thoroughly ground in a suitable mill, affording wettable powders which can be diluted with water to give suspensions of the desired concentration.

| 2.8. Suspension concentrate | |
|---|---|
| a compound according to Preparatory Examples 1.2. | 40% |
| ethylene glycol | 10% |
| nonylphenol polyethylene glycol (15 mol of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

EXAMPLE 3

Biological Tests 3.1. Action against *Musca domestica*

A sugar lump is moistened with a solution of the test compound in an amount sufficient to give a concentration of 500 ppm of active ingredient in the dried lump. The treated sugar lump is placed in a dish together with a wet cotton wool swab and covered with a glass beaker. Ten adult one-week-old and OP-resistant flies are then placed beneath the beaker and kept at 25° C. and 50% humidity. The insecticidal activity is evaluated by determining mortality after 24 hours.

Compounds of Examples 1.2. exhibit good activity in this test.

3.2. Action against *Lucilia sericata*

1 ml of an aqueous solution containing 0.5% of test compound is added at 50° C. to 9 ml of a culture medium. Then about 30 freshly hatched Lucilia sericata larvae are added to the culture medium, and the insecticidal action is determined after 48 and 96 hours by evaluating the mortality rate.

In this test, compounds of Example 1.2. exhibit good activity against *Lucilia sericata*.

3.3. Action against ticks in various development stages

About 50 larvae, about 25 nymphs or about 10 imagines of each of the tick species *Rhipicephalus bursa*, *Amblyomma hebraeum* and *Boophilus microplus* are used as test organisms. The test organisms are immersed for a short time in aqueous emulsions containing the respective test compound in a concentration of 400 ppm. The emulsions, which are contained in test tubes, are then absorbed by cotton wool, and the wetted test organisms are left in the test tubes which have thus been contaminated. Evaluation is made 3 days later to determine larvicidal activity and 14 days later to determine activity against nymphs and imagines. Mortality is expressed in percent.

Compounds according to Examples 1.2. exhibit good activity in this test.

3.4. Stomach toxicant action against *Spodoptera littoralis* larvae $L_1$

Cotton plants in the cotyledon stage are sprayed with an aqueous emulsion (obtained from a 10% emulsifiable concentrate) containing 400 ppm of the test compound. After the spray coating has dried, each cotton plant is populated with *Spodoptera littoralis* larvae in the $L_1$-stage. The test is carried out at 26° C. and ca. 50% relative humidity. A mortality count is made after 2 and 3 days and, after 5 days, the larvae are examined for inhibition of development and moulting.

Compounds of Examples 1.2. exhibit good activity in this test.

3.5. Stomach poison action against *Spodoptera littoralis* and *Heliothis virescens* larvae ($L_3$)

Potted soybean plants (pot size: 10 cm diameter) in the 4-leaf stage are sprayed with aqueous emulsions which contain the test compound in a concentration of 400 ppm.

After 2 days, each treated soybean plant is populated with 10 larvae of each of the species *Spodoptera littoralis* and *Heliothis virescens* in the $L_3$-stage. The test is carried out at 26° C. and ca. 60% relative humidity in dim light. After 2 and 5 days evaluation is made to determine the percentage mortality of the larvae.

Compounds of Examples 1.2. effect 80–100% kill.

3.6. Insecticidal stomach poison action against *Plutella xylostella* larvae ($L_2$)

Potted Chinese cabbage plants (pot size: 10 cm diameter) in the 4-leaf stage are sprayed with aqueous emulsions which contain the test compound in a concentration of 400 ppm.

After 2 days, each treated Chinese cabbage plant is populated with 10 *Plutella xylostella* larvae in the $L_2$-stage. The test is carried out at 26° C. and ca. 60% relative humidity in dim light. After 2 and 5 days evaluation is made to determine the percentage mortality of the larvae.

Compounds of Examples 1.2. effect 80–100% kill.

3.7. Contact action against *Nilaparvata lugens* (nymphs)

The test is carried out with growing plants. For this purpose 4 rice plants (ca. 20 days old), about 15 cm in height, are planted into each of a number of pots (diameter 5.5 cm). The plants in each pot are sprayed on a rotary table with 40 ml of an acetonic solution containing 400 ppm of the respective test compound. After the spray coating has dried, each plant is populated with 20 nymphs of the test organisms in the second or third stage. To prevent the cicadas from escaping, a glass cylinder is slipped over each of the plants and sealed with a gauze top. The nymphs are kept for 6 days on the treated plant, which has to be watered again at least once. The test is carried out at about 23° C. and 55% relative humidity and the plants are exposed to light for 16 hours.

Compounds of Examples 1.2. exhibit good activity in this test.

3.8. Systemic action against *Nilaparvata lugens*

Rice plants which are about 10 days old and about 10 cm high are put into a plastic beaker which contains 20 ml of an aqueous emulsion formulation of the test compound in a concentration of 100 ppm and which is sealed with a perforated plastic lid. The root of each rice plant is pushed through a hole in the plastic lid into the aqueous test formulation. The perforation is sealed with cottonwool in order to fix the plant and to protect the test organisms from contact with the gas phase. The rice plant is then populated with 20 nymphs of *Nilaparvata lugens* in the $N_2$–$N_3$ stage and covered with a plastic cylinder. The test is carried out at 26° C. and ca. 60% relative humidity and the plant is exposed to light for 16 hours. A mortality count is made 2 and 5 days later, using untreated controls for comparison purposes, thereby establishing whether the test compound absorbed through the root kills the test organisms on the upper parts of the plant.

Compounds of Examples 1.2. effect 80–100% kill of *Nilaparvata lugens* in this test.

3.9. Action against soil insects (*Diabrotica balteata*)

350 ml of soil (consisting of 95 vol. % of sand and 5 vol. % of peat) are mixed with 150 ml of an aqueous emulsion formulation which contains the test compound in a concentration of 400 ppm. Plastic beakers with a diameter of about 10 cm at the top are then partly filled with the treated soil. Ten $L_3$-larvae of *Diabrotica balteata* are put into each beaker, then 4 maize seedlings are planted and the beaker is filled up with soil. The beakers are sealed with plastic sheeting and kept at about 24° C. amd ca. 50% relative humidity. Six days later the soil in the beakers is sieved and a mortality count of the remaining larvae is made.

Compounds of Examples 1.2. exhibit good activity in this test.

3.10. Contact action against *Aphis craccivora*

Before the start of the test, 4- to 5-day old pea seedlings (*Pisum sativum*) grown in pots are each populated with about 200 insects of the species *Aphis craccivora*. The treated plants are sprayed direct to drip point 24 hours later with an aqueous formulation containing 400 ppm of the test compound. Two plants are used for each test compound. A mortality count is made after 3 and after 5 days. The test is carried out at ca. 21° C. and at a relative humidity of about 55%.

Compounds of Examples 1.2. exhibit good activity in this test.

3.11. Contact action against *Myzus persicae*

4- to 5-day old pea seedlings (*Pisum sativum*) which have been cultivated in water are each populated with about 200 aphids of the species *Myzus persicae* before the start of the test. The treated plants are sprayed direct to drip point 24 hours later with an aqueous suspension containing the test compound in a concentration of 100 ppm. Two plants are used for each compound. An evaluation of percentage mortality is made 3 and 5 days after application. The test is carried out at ca. 21° C. and ca. 60% relative humidity.

Compounds of Examples 1.2. exhibit good activity in this test.

3.12. Action against *Tetranychus urticae* (OP-sensitive)

24 hours before the test for acaricidal action, the primary leaves of *Phaseolus vulgaris* plants are infected with an infested piece of leaf from a mass culture of *Tetranychus urticae* (OP-sensitive) (mixed population). The tolerance refers to the tolerance to diazinone. The treated infested plants are sprayed to drip point with a test solution in emulsion form containing the respective test compound in a concentration of 400 ppm. During the test run the plants are kept in greenhouse compartments at ca. 25° C. and ca. 50% relative humidity. A count of the number of living and dead imagines and larvae (all mobile stages) is made under a stereoscopic microscope after 6 days.

Compounds of Examples 1.2. exhibit good activity in this test.

3.13. Action against *Panonychus ulmi* (OP and carbamate-resistant)

Potted apple seedlings with about 20 to 30 leaves are each populated with 60 adult females of *Panonychus ulmi*. The infested plants are sprayed after 7 days to drip point with an aqueous emulsion containing 100 ppm of the test compound. The treated plants are then stood in a greenhouse for a further 14 days at ca. 25° C. and about 50% relative humidity.

After this time, evaluation is made by taking 20 leaves from each plant, removing the mite population from these leaves by means of a brushing device and counting the number of eggs, postembryonic stages and adults under a stereoscopic microscope. An assessment is made of the percentage reduction of the mite population compared with untreated controls.

Compounds of Examples 1.2. exhibit good activity in this test.

3.14. Action against *Anthonomus grandis* (adults)

Two cotton plants in the 6-leaf stage, in pots, are each sprayed with a wettable aqueous emulsion formulation containing 100 ppm of the test compound. After the spray coating has dried (about 1½ hours), each plant is populated with 10 adult beetles (*Anthonomus grandis*). Plastic cylinders, covered at the top with gauze, are then slipped over the treated plants populated with the test insects to prevent the beetles from migrating from the plants. The treated plants are then kept at 25° C. and about 60% relative humidity. Evaluation is made after 2, 3, 4 and 5 days to determine the percentage mortality of the beetles (percentage in dorsal position) as well as the anti-feeding action as compared with untreated controls.

Compounds of Example 1.2. exhibit good activity in this test.

3.15. Action against *Dermanyssus gallinae*

2 to 3 ml of a solution containing 100 ppm of test compound and ca. 200 mites in different development stages are put into a glass container which is open at the top. The container is then sealed with cotton wool, shaken for 10 minutes until the mites are thoroughly wetted, and then briefly held upside down so that the remainder of the test solution can be absorbed by the cotton wool. A morality count is made after 3 days and the result expressed in percent.

Compounds of Examples 1.2. effect 80–100% kill.

3.16. Action against sensitive and resistant adults of *Bemisia tabaci*

Cotton leaves are immersed in a test solution containing 400 ppm of the test compound. The treated, dry leaves are placed in covered petri dishes and populated with 20–50 sensitive and resistant adults of *Bemisia tabaci*. A mortality count is made 24 hours later.

Compounds of Examples 1.2. exhibit good activity in this test.

3.17. Ovicidal action against *Tetranychus cinnabarinus*

Dwarf beans in the 2-leaf stage are populated, for oviposition, with adults females (20 per leaf) of an OP-tolerant strain of *Tetranychus cinnabarinus*. Twenty-four hours later, when 50 to 100 at most 24-hour-old eggs are present on the test plant, the females are removed and the plants are sprayed to drip point in a spray compartment with an aqueous formulation of the test compound (obtained from a 20% wettable powder)

at a concentration of 200 ppm. A mortality count is made 6 days later. The test is carried out at ca. 25° C. and ca. 50% relative humidity.

Compounds of Examples 1.2. exhibit good activity in this test.

What is claimed is:

1. A compound of formula I

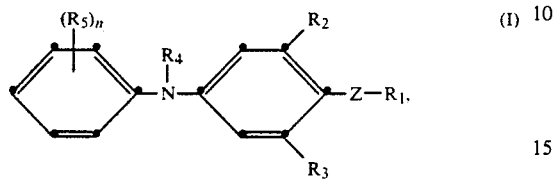

wherein
R₁ is C₁-C₁₂alkyl, unsubstituted or substituted by one or more halogen atoms and/or C₁-C₆alkoxy groups; C₃-C₈cycloalkyl, unsubstituted or substituted by one or more C₁-C₃alkyl groups; or C₃-C₈cycloalkyl C₁-C₄alkyl,
R₂ and R₃ are each C₁-C₅alkyl or C₅-C₆cycloalkyl,
R₄ is hydrogen, methyl or —CHO,
R₅ is halogen; C₁-C₄alkyl, unsubstituted or substituted by one or more halogen atoms; C₁-C₄alkoxy, unsubstituted or substituted by one or more halogen atoms; or is a —(CH=CH)₂, —(CH₂)₃ or —(CH₂)₄ bridge in 2,3- or 3,4-position,
n is 0, 1, 2, 3 or 4, and
Z is —NH—CS—NH—,
or a salt thereof with an organic or inorganic acid.

2. A compound of formula I according to claim 1, wherein R₁ is C₁-C₈alkyl unsubstituted or substituted by one or more halogen atoms and/or C₁-C₅alkoxy groups, or is C₃-C₈cycloalkyl; R₂ is C₁-C₅alkyl; R₃ is C₁-C₅alkyl or C₅-C₆cycloalkyl; R₄ is hydrogen, methyl or —CHO; R₅ is halogen, C₁-C₃alkyl or a —(CH=CH)₂ or —(CH₂)₃ bridge in 3,4-position; n is 0, 1 or 2 and Z is —NH—CS—NH—.

3. A compound of formula I according to claim 2, wherein R₁ is C₁-C₅alkyl or cyclopentyl; R₂ and R₃ are each C₁-C₄alkyl; R₄ is hydrogen, methyl or —CHO; R₅ is methyl; n is 0 or 1; and Z is —NH—CS—NH—.

4. A compound according to claim 1 of formula

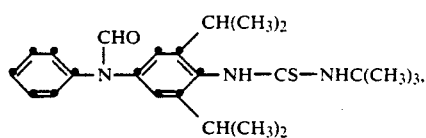

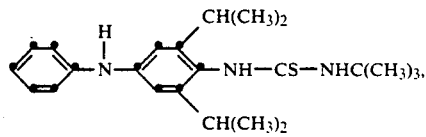

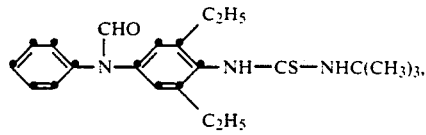

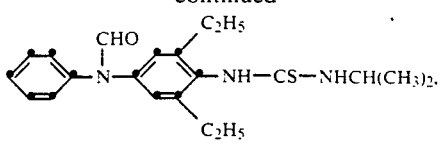

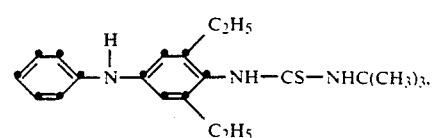

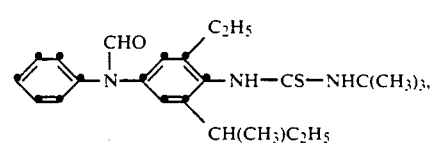

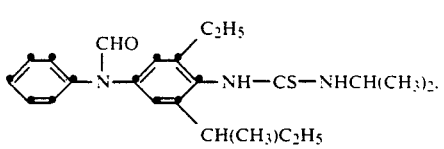

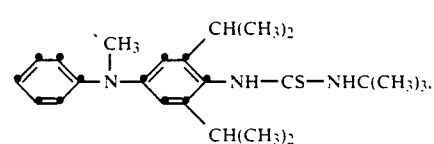

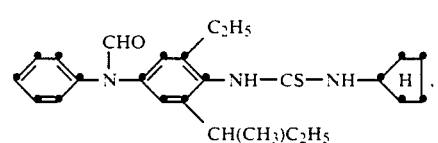

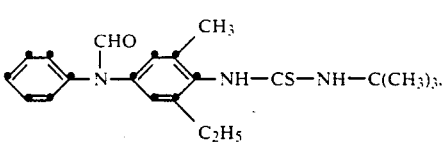

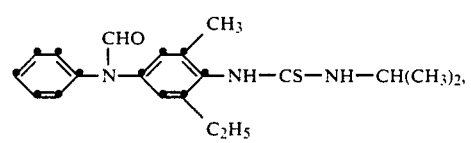

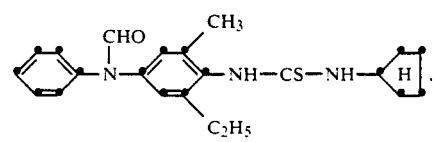

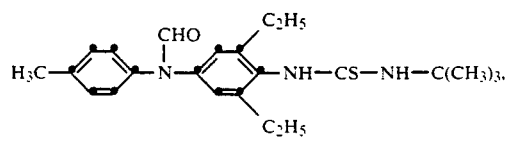

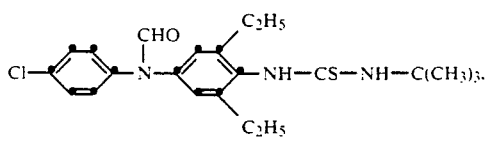

-continued

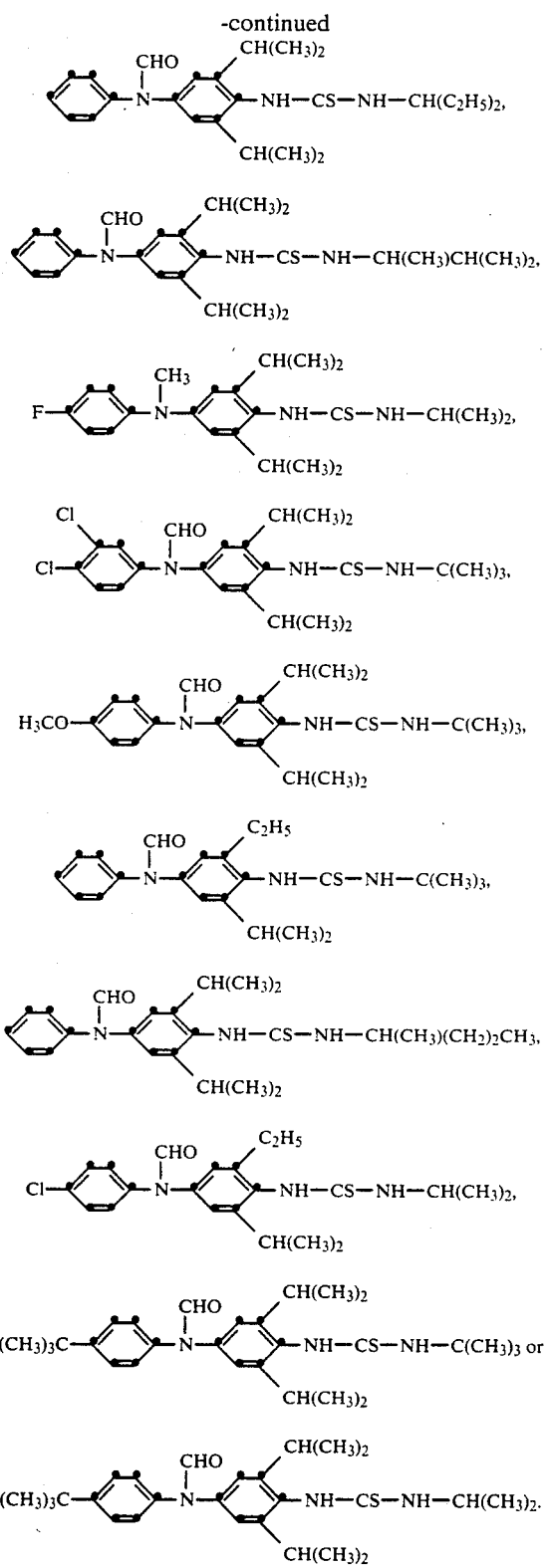

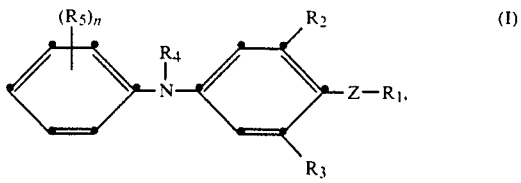

5. A pesticidal composition which comprises, as active component, an insecticidally and arachnidicidally effective amount of a compound of formula I wherein
$R_1$ is $C_1$-$C_{12}$alkyl, unsubstituted or substituted by one or more halogen atoms and/or $C_1$-$C_6$alkoxy groups; $C_3$-$C_8$cycloalkyl, unsubstituted or substituted by one or more $C_1$-$C_3$alkyl groups; or $C_3$-$C_8$-cycloalkyl$C_1$-$C_4$alkyl,
$R_2$ and $R_3$ are each $C_1$-$C_5$alkyl or $C_5$-$C_6$cycloalkyl,
$R_4$ is hydrogen, methyl or —CHO,
$R_5$ is halogen; $C_1$-$C_4$alkyl, unsubstituted or substituted by one or more halogen atoms; $C_1$-$C_4$alkoxy, unsubstituted or substituted by one or more halogen atoms; or is a $-(CH=CH)_2$, $-(CH_2)_3$ or $-(CH_2)_4$ bridge in 2,3- or 3,4-position,
n is 0, 1, 2, 3 or 4, and
Z is —NH—CS—NH—,
or a salt thereof with an organic or inorganic acid, together with suitable carriers and/or adjuvants.

6. A pesticidal composition according to claim 5 which comprises, as active component, a compound of formula I, wherein $R_1$ is $C_1$-$C_8$alkyl, unsubstituted or substituted by one or more halogen atoms and/or $C_1$-$C_5$alkoxy groups, or is $C_3$-$C_8$cycloalkyl; $R_2$ is $C_1$-$C_5$alkyl; $R_3$ is $C_1$-$C_5$alkyl or $C_5$-$C_6$cycloalkyl; $R_4$ is hydrogen, methyl or —CHO; $R_5$ is halogen, $C_1$-$C_3$alkyl or a —CH=CH—$_2$ or —CH$_2$—$_3$ bridge in 3,4-position; n is 0, 1 or 2 and Z is —NH—CS—NH—.

7. A pesticidal composition according to claim 6, wherein $R_1$ is $C_1$-$C_5$alkyl or cyclopentyl; $R_2$ and $R_3$ are each $C_1$-$C_4$alkyl; $R_4$ is hydrogen, methyl or —CHO; $R_5$ is methyl; n is 0 or 1; and Z is —NH—CS—NH—.

8. A method of controlling pests of animals and plants selected from the group consisting of insects and arachnids, which comprises contacting said pests in their different development stages with an insecticidally and arachnidicidally effective amount of a compound of formula I

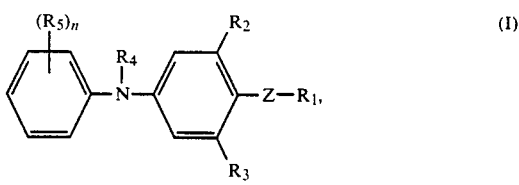

wherein
$R_1$ is $C_1$-$C_{12}$alkyl, unsubstituted or substituted by one or more halogen atoms and/or $C_1$-$C_6$alkoxy groups; $C_3$-$C_8$cycloalkyl, unsubstituted or substituted by one or more $C_1$-$C_3$alkyl groups; or $C_3$-$C_8$-cycloalkyl-$C_1$-$C_4$alkyl,
$R_2$ and $R_3$ are each $C_1$-$C_5$alkyl or $C_5$-$C_6$cycloalkyl,
$R_4$ is hydrogen, methyl or —CHO,
$R_5$ is halogen; $C_1$-$C_4$alkyl, unsubstituted or substituted by one or more halogen atoms; $C_1$-$C_4$alkoxy, unsubstituted or substituted by one or more halogen atoms; or is a —(CH=CH)$_2$—, —(CH$_2$)$_3$— or —(CH$_2$)$_4$— bridge in the 2,3- or 3,4-position,
n is 0, 1, 2, 3 or 4, and
Z is —NH—CS—NH—,
or with a salt thereof with an organic or inorganic acid.

* * * * *